(12) United States Patent
Leeflang et al.

(10) Patent No.: US 8,927,048 B2
(45) Date of Patent: Jan. 6, 2015

(54) APPARATUS AND METHODS FOR MAKING COATED LINERS AND TUBULAR DEVICES INCLUDING SUCH LINERS

(75) Inventors: Stephen A. Leeflang, Sunnyvale, CA (US); Christian S. Eversull, Palo Alto, CA (US)

(73) Assignee: Aust Development, LLC, Palo Alto, CA (US)

(*) Notice: Subject to any disclaimer, the term of this patent is extended or adjusted under 35 U.S.C. 154(b) by 565 days.

(21) Appl. No.: 12/708,526

(22) Filed: Feb. 18, 2010

(65) Prior Publication Data
US 2010/0206453 A1 Aug. 19, 2010

Related U.S. Application Data

(60) Provisional application No. 61/153,295, filed on Feb. 18, 2009, provisional application No. 61/223,352, filed on Jul. 6, 2009, provisional application No. 61/227,745, filed on Jul. 22, 2009, provisional application No. 61/234,311, filed on Aug. 16, 2009.

(51) Int. Cl.
| | |
|---|---|
| *A61L 33/00* | (2006.01) |
| *B29D 23/00* | (2006.01) |
| *B29C 61/00* | (2006.01) |
| *B29L 31/00* | (2006.01) |
| *B29C 53/42* | (2006.01) |
| *B29C 53/60* | (2006.01) |
| *A61M 25/00* | (2006.01) |
| *B29C 53/50* | (2006.01) |

(52) U.S. Cl.
CPC .......... *A61M 25/0009* (2013.01); *B29C 61/006* (2013.01); *B29L 2031/7542* (2013.01); *B29C 53/42* (2013.01); *B29C 53/60* (2013.01); *B29D 23/001* (2013.01); *A61M 25/0045* (2013.01); *B29C 53/50* (2013.01); *A61M 25/0012* (2013.01)
USPC ........... 427/2.24; 427/2.1; 427/230; 427/236; 427/289; 427/290; 427/421.1; 427/427.1

(58) Field of Classification Search
USPC ....... 128/207.14; 161/39; 148/563; 623/1.12, 623/1.11
See application file for complete search history.

(56) References Cited

U.S. PATENT DOCUMENTS

| | | | |
|---|---|---|---|
| 2,805,973 | A | 9/1957 | Klasing et al. |
| 3,269,278 | A | 8/1966 | Olstad |

(Continued)

FOREIGN PATENT DOCUMENTS

| | | |
|---|---|---|
| WO | 9113648 | 9/1991 |
| WO | 9620750 | 7/1996 |

(Continued)

OTHER PUBLICATIONS

International Publication No. WO 99/01281; Applicant: Thermon Manufacturing Company; 20 pages, 1999.

*Primary Examiner* — Dah-Wei D Yuan
*Assistant Examiner* — Andrew Bowman
(74) *Attorney, Agent, or Firm* — William A. English; Vista IP Law Group LLP

(57) ABSTRACT

Apparatus and methods are provided for making coated liners and/or tubular devices including such coated liners. A sleeve may be provided that includes an outer first surface and an inner second surface extending between first and second ends thereof, and a hydrophilic or other coating may be applied to the first. The coated sleeve may be cut between the first and second ends to create opposing edges extending between the first and second ends, and the cut sleeve may be reversed such that the coated first surface defines an inner surface and the opposing edges are disposed adjacent one another, thereby providing a coated liner. Optionally, a tubular structure, e.g., one or more reinforcing layers and/or or outer layers may be attached around the coated liner, thereby providing a tubular device including an inner surface with a desired coating.

23 Claims, 22 Drawing Sheets

(56) References Cited

U.S. PATENT DOCUMENTS

| | | | |
|---|---|---|---|
| 3,511,435 | A | 5/1970 | Cawley et al. |
| 3,540,959 | A | 11/1970 | Houghton |
| 3,770,556 | A * | 11/1973 | Evans et al. ............... 428/77 |
| 3,879,516 | A | 4/1975 | Wolvek |
| 4,478,898 | A | 10/1984 | Kato |
| 4,516,972 | A | 5/1985 | Samson |
| 4,636,346 | A | 1/1987 | Gold et al. |
| 4,863,442 | A | 9/1989 | DeMello et al. |
| 5,047,045 | A | 9/1991 | Arney et al. |
| 5,176,661 | A | 1/1993 | Evard et al. |
| 5,217,440 | A | 6/1993 | Frassica |
| 5,254,107 | A | 10/1993 | Soltesz |
| 5,305,740 | A * | 4/1994 | Kolobow ............... 128/207.14 |
| 5,370,655 | A | 12/1994 | Burns |
| 5,400,785 | A | 3/1995 | Crowley |
| 5,447,497 | A | 9/1995 | Sogard et al. |
| 5,514,236 | A | 5/1996 | Avellanet et al. |
| 5,549,109 | A | 8/1996 | Samson et al. |
| 5,569,221 | A | 10/1996 | Houser et al. |
| 5,676,659 | A | 10/1997 | McGurk |
| 5,713,867 | A | 2/1998 | Morris |
| 5,735,809 | A | 4/1998 | Gorsuch |
| 5,811,043 | A | 9/1998 | Horrigan et al. |
| 5,836,926 | A | 11/1998 | Peterson et al. |
| 5,967,988 | A | 10/1999 | Briscoe et al. |
| 6,004,310 | A | 12/1999 | Bradsley et al. |
| 6,027,779 | A | 2/2000 | Campbell et al. |
| 6,177,523 | B1 | 1/2001 | Reich et al. |
| 6,183,443 | B1 | 2/2001 | Kratoska et al. |
| 6,217,566 | B1 | 4/2001 | Ju et al. |
| 6,293,907 | B1 | 9/2001 | Axon et al. |
| 6,310,244 | B1 | 10/2001 | Tran et al. |
| 6,315,792 | B1 | 11/2001 | Armstrong et al. |
| 6,511,462 | B1 | 1/2003 | Itou et al. |
| 6,592,576 | B2 | 7/2003 | Andrews et al. |
| 6,669,886 | B1 | 12/2003 | Willard |
| 6,830,568 | B1 | 12/2004 | Kresten et al. |
| 6,837,890 | B1 | 1/2005 | Chludzinski et al. |
| 6,843,802 | B1 * | 1/2005 | Villalobos et al. ........... 623/1.12 |
| 6,942,654 | B1 | 9/2005 | Schaefer et al. |
| 6,945,970 | B2 | 9/2005 | Pepin |
| 6,946,173 | B2 | 9/2005 | Lim et al. |
| 6,979,290 | B2 | 12/2005 | Mourlas |
| 7,188,623 | B2 | 3/2007 | Anderson et al. |
| 7,273,469 | B1 | 9/2007 | Chan et al. |
| 7,306,585 | B2 | 12/2007 | Ross |
| 7,520,950 | B2 | 4/2009 | Saadat et al. |
| 7,553,387 | B2 | 6/2009 | Leeflang et al. |
| 8,187,396 | B2 * | 5/2012 | Parker ........................ 148/563 |
| 2001/0016702 | A1 | 8/2001 | Benjamin |
| 2001/0053931 | A1 | 12/2001 | Hess et al. |
| 2002/0156494 | A1 | 10/2002 | Simhambhatla et al. |
| 2003/0233115 | A1 | 12/2003 | Eversull et al. |
| 2005/0059957 | A1 | 3/2005 | Campbell et al. |
| 2005/0085841 | A1 | 4/2005 | Eversull et al. |
| 2005/0085842 | A1 | 4/2005 | Eversull et al. |
| 2005/0149104 | A1 | 7/2005 | Leeflang et al. |
| 2005/0197623 | A1 | 9/2005 | Leeflang et al. |
| 2005/0228452 | A1 | 10/2005 | Mourlas et al. |
| 2007/0074805 | A1 | 4/2007 | Leeflang et al. |
| 2007/0075452 | A1 | 4/2007 | Leeflang et al. |
| 2007/0088296 | A1 | 4/2007 | Leeflang et al. |
| 2007/0169877 | A1 | 7/2007 | Leeflang et al. |
| 2009/0126862 | A1 | 5/2009 | Leeflang et al. |
| 2009/0227962 | A1 | 9/2009 | Eversull et al. |

FOREIGN PATENT DOCUMENTS

| | | | |
|---|---|---|---|
| WO | 9740880 | 11/1997 | |
| WO | 9851370 | 11/1998 | |
| WO | 9937350 | 7/1999 | |
| WO | WO 00/18446 * | 4/2000 | ............. A61L 29/00 |
| WO | 0107101 | 2/2001 | |
| WO | 03020353 | 3/2003 | |
| WO | 2004075961 | 9/2004 | |

* cited by examiner

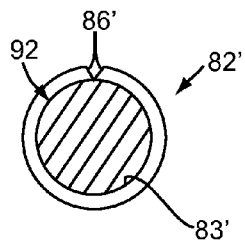
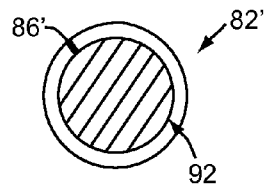
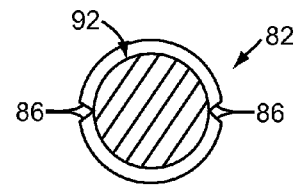
FIG. 8A  FIG. 9A  FIG. 10A
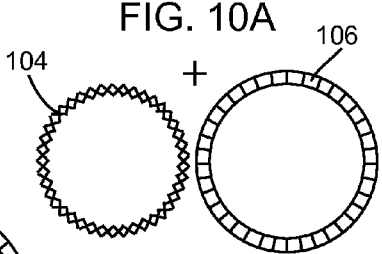
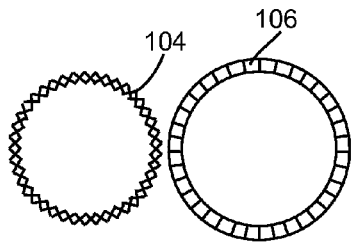
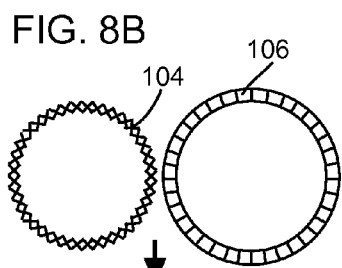
FIG. 8B  FIG. 9B  FIG. 10B
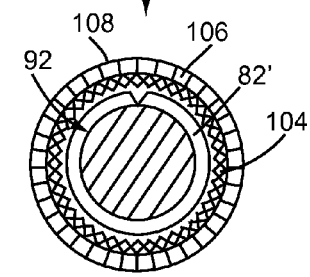
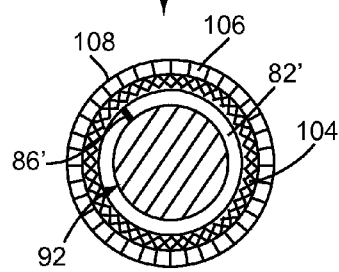
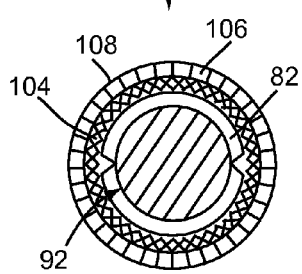
FIG. 8C  FIG. 9C  FIG. 10C
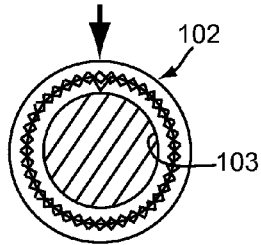
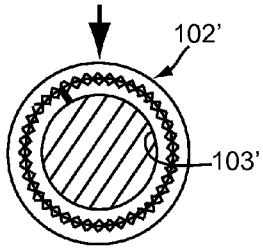
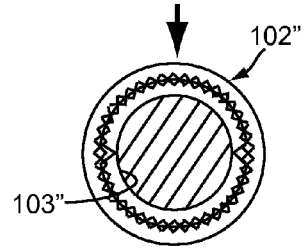
FIG. 8D  FIG. 9D  FIG. 10D

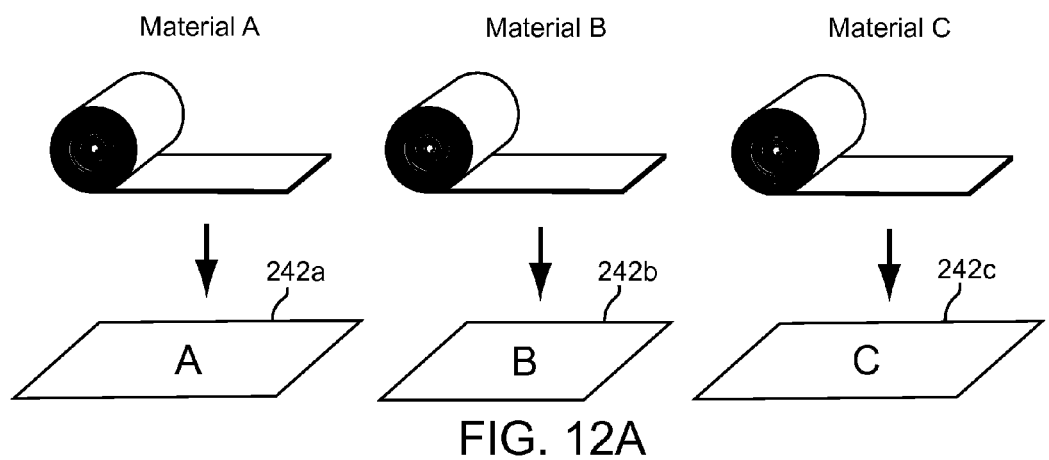
FIG. 12A
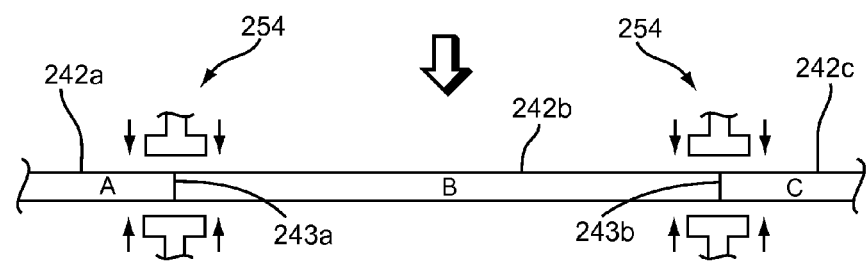
FIG. 12B
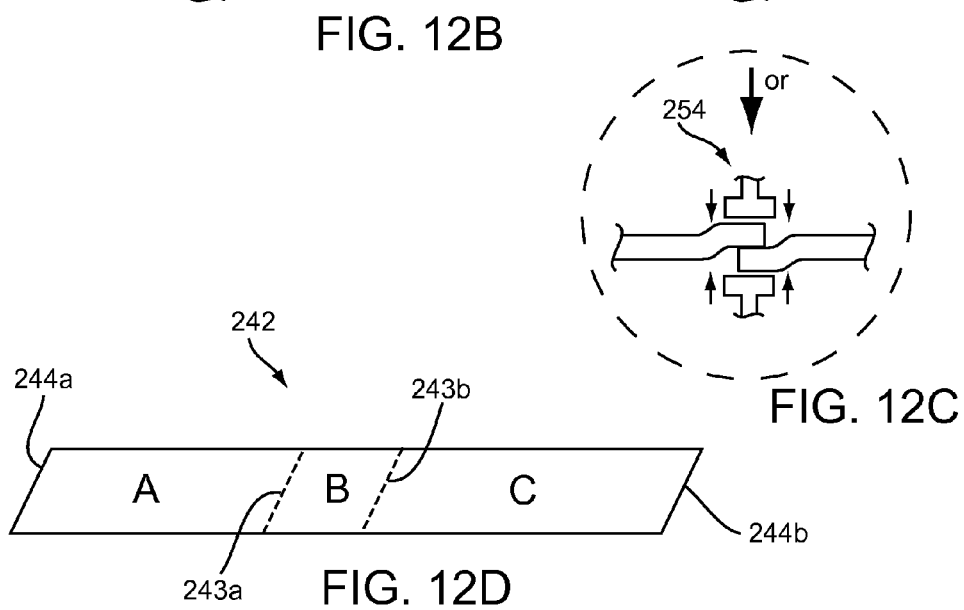
FIG. 12C
FIG. 12D

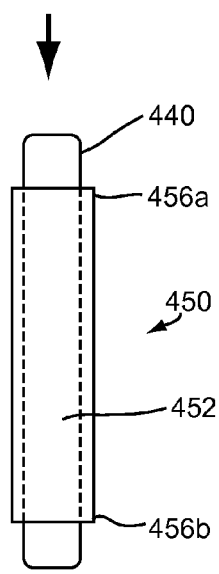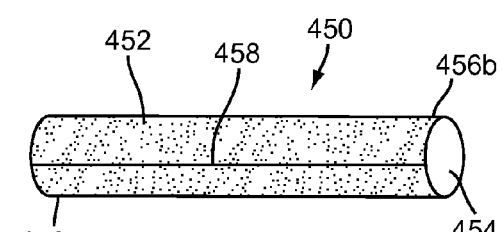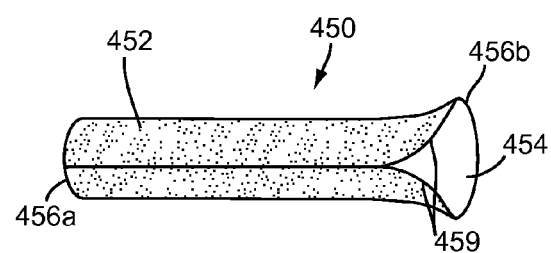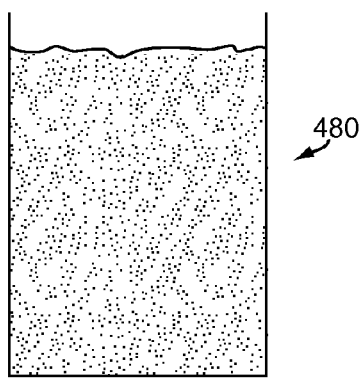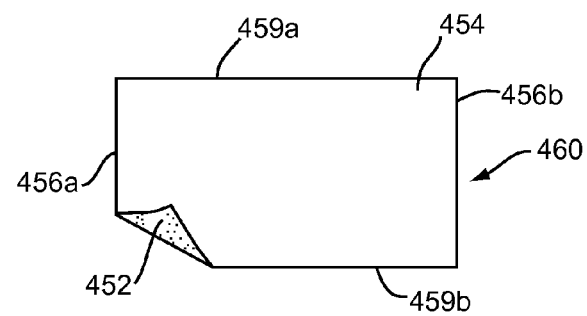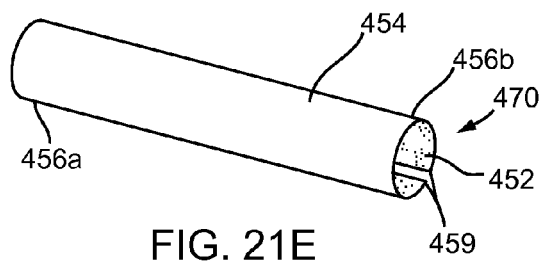
FIG. 21A
FIG. 21B
FIG. 21C
FIG. 21D
FIG. 21E

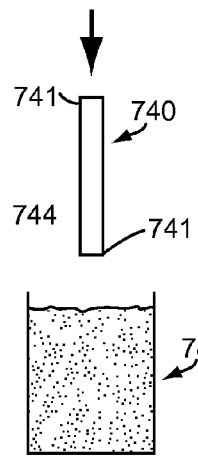
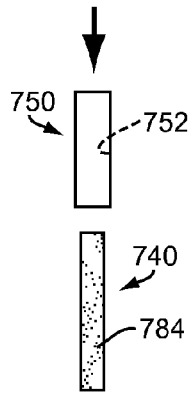
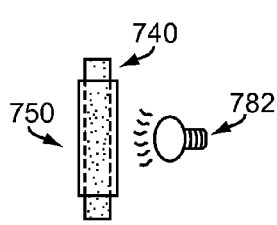
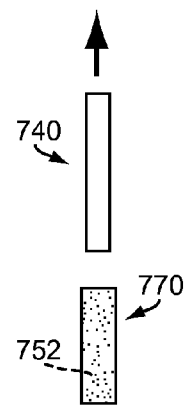
FIG. 28A  FIG. 28B  FIG. 28C  FIG. 28D
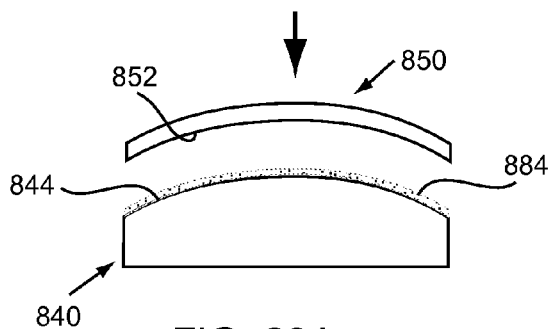
FIG. 29A
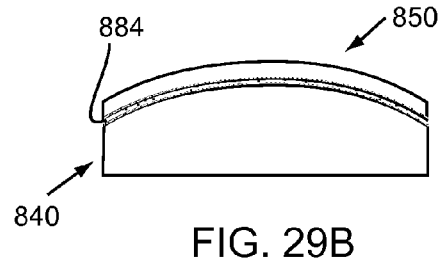
FIG. 29B
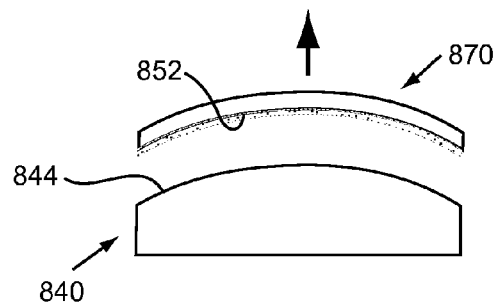
FIG. 29C

APPARATUS AND METHODS FOR MAKING COATED LINERS AND TUBULAR DEVICES INCLUDING SUCH LINERS

This application claims benefit of provisional application Ser. Nos. 61/153,295, filed Feb. 18, 2009, 61/223,352, filed Jul. 6, 2009, 61/227,745, filed Jul. 22, 2009, and 61/234,311, filed Aug. 16, 2009, the entire disclosures of which are expressly incorporated by reference herein.

FIELD OF THE INVENTION

The present invention relates generally to apparatus and methods for making catheters, sheaths, or other tubular devices, and, more particularly, to apparatus and methods for making coated liners for catheters, sheaths, or other tubular devices, and catheters, sheaths, or other tubular devices including coated liners.

BACKGROUND

Medical devices, such as catheters, sheaths, or other tubular devices, frequently have one or more inner lumens that partially or fully extend through the device. These lumens are routinely exposed to bodily fluids or tissues and/or interact with other instruments and/or physician specified fluids unique to a given device or procedure. Given the disparate uses of these lumens and subsequent wide variety in desired performance attributes, various materials and processes have been developed and explored to impart desired performance attributes. In spite of a wide variety of materials, including specialty coatings, the processes currently known for constructing catheters including desired performance attributes are generally limited and are frequently prohibitively complicated and/or expensive. For example, applying an anti-thrombogenic coating to the inner surface of a cardiovascular catheter device or subassembly may require 1) masking undesired parts of the catheter from exposure to the coating and/or 2) special curing processes like exposure to heat or Ultraviolet ("UV") light. However, heat may be damaging to other catheter components and/or it may be difficult to expose inner surfaces of small lumens to UV light even over modest lengths. Alternatively, constructions may include lubricious liners and/or hydrophilic coatings. These tedious processes, however, routinely exact compromises that reduce the effectiveness of the materials used or applied. Furthermore, these processes do not lend themselves to batch or mass production and therefore lack the associated benefits in cost and quality.

SUMMARY

The present invention is directed to apparatus and methods for making catheters, sheaths, or other tubular devices. More particularly, the present invention is directed to apparatus and methods for making coated liners for catheters, sheaths, or other tubular devices, and tubular devices including such coated liners.

In accordance with one embodiment, a tubular device is provided that includes a proximal end, a distal end sized for introduction into a body lumen, and a lumen extending between the proximal and distal ends. Generally, the tubular device includes an inner liner including a coating on an inner surface thereof, the coating imparting one or more predetermined properties to a wall of the lumen, a reinforcing layer surrounding at least a portion of the liner; and an outer layer surrounding the reinforcing layer and inner liner.

In one embodiment, the liner may include multiple sections having different properties than one another, adjacent sections being attached together by seams, and the outer layer may also include multiple sections having different properties than one another. If desired, the adjacent sections of the outer layer may be attached together by seams that are spaced apart axially from seams of the inner liner, e.g., to stagger the seams and/or provide smoother transitions on the distal end of the tubular member.

Optionally, the tubular device may include a distal tip attached to the distal end of the tubular device, the distal tip including an outer tubular layer surrounding a coated liner without a reinforcing layer. The materials of the distal tip may have different properties than the multiple sections of the inner liner and outer layer, e.g., having Durometers that are substantially softer than the adjacent sections of the distal end of the tubular device. For example, in one embodiment, the coated liner of the distal tip may comprise material that is softer than a distal-most section of the inner liner of the distal end and/or the outer tubular layer of the distal tip may comprise material that is softer than a distal-most section of the outer layer of the distal end.

In addition or alternatively, the multiple sections of the inner liner may include a relatively soft distal-most section and a relatively less soft shaft section attached to the distal-most section by a first seam. The first seam may be substantially orthogonal or non-orthogonal to a longitudinal axis of the tubular device. Alternatively, the first seam may include edges of the distal-most section and the shaft section that are interlocked with one another.

Similarly, the multiple sections of the outer layer may include a plurality of transition sections adjacent one another on the distal end and a shaft section that extends proximally from the transition sections. For example, the transition sections may include a first distal-most transition section, and a second transition section attached to the first transition section, the first transition section having a lower Durometer than the second transition section. Optionally, the transition sections may also include a third transition section attached between the second transition section and the shaft section, the second transition section having a lower Durometer than the third transition section.

In an exemplary embodiment, the multiple sections of the inner liner may comprise different color materials, e.g., to facilitate identifying transitions between the multiple sections.

In accordance with another embodiment, a tubular device is provided that includes a proximal end, a distal end sized for introduction into a body lumen, and a lumen extending between the proximal and distal ends. The tubular device may include an inner liner including a coating on an inner surface thereof, the coating imparting one or more predetermined properties to a wall of the lumen, a reinforcing layer surrounding at least a portion of the liner, and an outer layer surrounding the reinforcing layer and inner liner. The inner liner may include multiple sections attached together, wherein the multiple sections comprises different color materials to facilitate identifying transitions between the multiple sections, different Durometers, and/or different thicknesses.

In accordance with yet another embodiment, a tubular device is provided that includes a proximal end, a distal end sized for introduction into a body lumen, a lumen extending between the proximal and distal ends, and a distal tip attached to the distal end. The tubular device includes an inner liner comprising a coating on an inner surface thereof, the coating imparting one or more predetermined properties to a wall of the lumen. The liner also includes a transition section extending proximally from the distal tip, and a shaft section attached to the transition section, the transition section having different properties than the shaft section. In addition, the tubular device includes a reinforcing layer surrounding the liner; and an outer layer surrounding the reinforcing layer and inner liner. The outer layer may include one or more transition sections extending proximally from the distal tip and a shaft section attached to a proximal-most of the one or more transition sections. The distal tip may include an outer tubular layer surrounding a coated liner without a reinforcing layer, the material of the distal tip being softer than the transition sections of the inner liner and outer layer.

Optionally, the transition and shaft sections of the inner liner may be attached together at a seam, and adjacent sections of the outer layer may be attached together by seams that are spaced apart axially from seam of the inner liner. In addition or alternatively, the transition section of the inner liner may be softer than the shaft section of the inner liner, and/or the one or more transition sections of the outer layer may be softer than the shaft section.

In accordance with still another embodiment, a tubular device is provided that includes a proximal end, a distal end sized for introduction into a body lumen, and a lumen extending between the proximal and distal ends. The tubular device includes an inner liner comprising a coating on an inner surface thereof, the coating imparting one or more predetermined properties to a wall of the lumen. The inner liner may be formed from an enclosed band wrapped around a mandrel such that the inner liner defines a pair of longitudinal seams extending between the proximal and distal ends of the tubular device. In addition, the tubular device includes a reinforcing layer surrounding the liner; and an outer layer surrounding the reinforcing layer and inner liner.

Optionally, the enclosed band may include multiple sections having different properties such that the properties of the inner liner vary between the proximal and distal ends of the tubular device. In addition or alternatively, the outer layer may also include multiple sections having different properties than one another, adjacent sections being attached together by seams that are spaced apart axially from one or more seams separating the multiple sections of the inner liner.

In one embodiment, the longitudinal seams of the inner liner may extend substantially axially between the proximal and distal ends of the tubular device. Alternatively, the longitudinal seams of the inner liner extend helically between the proximal and distal ends of the tubular device. The longitudinal seams of the inner liner may include longitudinal edges that are spaced apart from one another to define gaps when the endless band is wrapped around the mandrel, the outer layer being reflowed to substantially fill the gaps between the longitudinal edges.

In accordance yet another embodiment, a method is provided for making a tubular device sized for introduction into a body lumen. An endless band of material including a coated surface may be folded such that the endless band defines first and second ends and the coated surface is disposed inwardly. The first and second ends of the endless band may be stretched or otherwise provided over opposite ends of an elongate mandrel such that the coated surface is disposed inwardly towards the mandrel and the endless band wraps partially around the mandrel such that longitudinal edges of the endless band extend between the opposite ends of the mandrel. A tubular structure may be attached around the endless band while wrapped around the mandrel, e.g., including a reinforcing layer and an outer tubular layer.

After attaching the tubular structure around the wrapped band, the enclosed ends of the endless band may be removed and/or the mandrel may be removed from the band to provide a tubular device defining a coated lumen.

In an exemplary embodiment, the endless band may be created by attaching first and second ends of a sheet together, mounting the resulting assembly to a coating apparatus, and applying a coating to at least one surface of the sheet.

In accordance with still another embodiment, a method is provided for making a tubular device sized for introduction into a body lumen that includes mounting an endless band to an apparatus that moves the band along an enclosed path including one or more coating elements; applying a coating to at least one of the inner surface and the outer surface using the one or more coating elements; and separating the endless band into a plurality of narrower endless bands after applying the coating.

One of the narrower bands may be folded such that the narrower endless band defines first and second ends and the coating is disposed inwardly. The first and second ends of the narrower band may be stretched or otherwise positioned over opposite ends of an elongate mandrel such that the coating is disposed inwardly towards the mandrel and the narrower endless band wraps partially around the mandrel such that longitudinal edges of the narrower endless band extend between the opposite ends of the mandrel. A tubular structure may then be attached around the narrower endless band while wrapped around the mandrel.

In accordance with another embodiment, a method is provided for making a tubular device sized for introduction into a body lumen that includes providing a sheet of material having first and second ends and longitudinal edges extending between the first and second ends, and attaching the first and second ends of the sheet together to create an endless band including an inner surface and an outer surface. The endless band may be mounted to an apparatus that moves the band along an enclosed path including one or more coating elements, and a coating may be applied to at least one of the inner surface and the outer surface using the one or more coating elements.

In one exemplary embodiment, the coating apparatus may include a drum including at least one of an interior surface and an exterior surface defining the enclosed path, and the endless band may be mounted to one of the interior and exterior surfaces of the drum. The coating may then be applied by rotating the drum to move the endless band past the one or more coating elements.

In another exemplary embodiment, the coating apparatus may include a roller assembly including a plurality of rollers defining the enclosed path, and the endless band may be mounted to the apparatus by extending the endless band between the plurality of rollers. The coating may then be applied by rotating one or more of the plurality of rollers to move the endless band along the enclosed path and past the one or more coating elements.

After coating, the endless band may then be separated into one or more liner components. For example, in one embodiment, the endless band may be cut or otherwise separated into one or more strips, and one of the strips may be wrapped around a mandrel such that the coating is disposed inwardly towards the mandrel. A tubular structure may then be attached around the wrapped strip and mandrel.

For example, ends of the strip may be secured to ends of the mandrel, and the strip may be wrapped around the mandrel in a longitudinal configuration, wherein longitudinal edges of the strip extend between the ends of the mandrel, e.g., in a longitudinal configuration. Alternatively, the strip may be wrapped helically around the mandrel between first and second ends of the mandrel.

In accordance with still another embodiment, a method is provided for making a tubular device sized for introduction into a body lumen that includes providing a sheet of material having first and second ends and longitudinal edges extending between the first and second ends; attaching the first and second ends of the sheet together to create an endless band including an inner surface and an outer surface; mounting the endless band to an apparatus that moves the band along an enclosed path including one or more coating elements; and applying a coating to at least one of the inner surface and the outer surface using the one or more coating elements. The endless band may be separated into a plurality of narrower bands after applying the coating, and each of the narrower bands may be wrapped around a mandrel such that the coating is disposed inwardly towards the mandrel and longitudinal edges of the band extend between ends of the mandrel. A tubular structure may then be attached around each of the wrapped bands.

In accordance with yet another embodiment, a method is provided for making a tubular device sized for introduction into a body lumen that includes providing a sheet of material having first and second ends and longitudinal edges extending between the first and second ends; attaching the first and second ends of the sheet together to create an endless band including an inner surface and an outer surface; mounting the endless band to an apparatus that moves the band along an enclosed path including one or more coating elements; and applying a coating to at least one of the inner surface and the outer surface using the one or more coating elements. The endless band may then be separated into one or more liner components after applying the coating, and each of the liner components may be wrapped around a mandrel such that the coating is disposed inwardly towards the mandrel. A tubular structure may then be attached around each of the wrapped liner components.

In accordance with still another embodiment, a method is provided for making one or more liner components for tubular devices sized for introduction into a body lumen. Initially, a plurality of endless bands may be provided, and a coating may be applied to at least a first surface of each of the endless bands. Optionally, at least one of the endless bands may be formed from a different material than one or more other endless bands and/or the coating applied to at least one of the endless bands may be different from a coating applied to one or more other endless bands. Each of the endless bands may be cut or otherwise separated into one or more sheets after applying a coating to each of the endless bands. At least one sheet from each of the endless bands may be attached together to create a composite sheet, and the composite sheet may be used to create a composite liner for a tubular device. For example, the composite sheet may be wrapped at least partially around a mandrel (alone or along with other composite sheets) to create a liner component, and a tubular structure may then be attached around the wrapped composite sheet.

In accordance with another embodiment, a tubular device is provided for aspiration of material from a body lumen that includes a proximal end, a distal end sized for introduction into a body lumen, an aspiration lumen extending between the proximal and distal ends, and a vacuum source coupled to the aspiration lumen. Generally, the tubular device includes an inner liner including a coating on an inner surface thereof, the coating adapted to decrease resistance to flow of aspirated material through the tubular device and/or decrease the propensity of aspirated material to clog the aspiration lumen.

In accordance with yet another embodiment, a tubular device is provided for aspiration of material from a body lumen that includes a proximal end, a distal end sized for introduction into a body lumen, an aspiration lumen extending between the proximal and distal ends, and a transport element within the aspiration lumen. Generally, the tubular device includes an inner liner including a coating on an inner surface thereof, the coating adapted to decrease resistance to flow of aspirated material through the tubular device and/or decrease the propensity of aspirated material to clog the aspiration lumen.

In accordance with still another embodiment, the tubular device for aspiration of material from a body lumen may include one or more macerating elements or cutting elements designed to macerate material to be aspirated from the body.

In accordance with still another embodiment, the tubular device may include a relatively smaller distal region adapted to track more easily through the vasculature, and a relatively larger proximal region adapted to maximize the diameter of an aspiration lumen.

In accordance with yet another embodiment, a method is provided for making a tubular device sized for introduction into a body lumen. Initially, a sleeve may be provided that includes a first outer surface and a second inner surface that extend between first and second ends of the sleeve. The first surface may be coated with a coating to impart the first surface with one or more desired properties, e.g., a hydrophilic material, an antithrombotic material, an antimicrobial material, an anti-hemolytic material, and/or a drug-eluting material.

The coated sleeve may be cut between the first and second ends to create opposing edges extending between the first and second ends, e.g., by creating a longitudinal seam that extends substantially parallel to a longitudinal axis of the sleeve. The longitudinal seam may extend partially or entirely through a wall of the sleeve and/or may extend continuously or intermittently between the first and second ends. The cut sleeve may then be reversed such that the coated first surface defines an inner surface of the reversed cut sleeve and the opposing edges are disposed adjacent one another.

Optionally, a tubular structure may be attached around the reversed cut sleeve, thereby providing a tubular device comprising an inner surface with the one or more desired properties. For example, in one embodiment, the reversed cut sleeve may be positioned over a mandrel such that the opposing edges are disposed adjacent one another, a tubular structure may be positioned over the reversed cut sleeve and mandrel, and the tubular structure may be attached to the reversed cut sleeve, e.g., by heating to reflow material of the sleeve and/or tubular structure, by bonding with adhesive, and the like. In an exemplary embodiment, the tubular structure may include a reinforcing layer applied around the reversed cut sleeve and one or more layers of material applied around the reinforcing layer.

In accordance with still another embodiment, a substantially continuous method is provided for making tubular devices sized for introduction into a body lumen. Initially, a sleeve may be provided that includes a first outer surface and a second inner surface that extend between first and second ends of the sleeve. For example, the sleeve may be provided on a supply mandrel, e.g., carried by a supply reel or other supply sources. The first surface may be coated with a coating, e.g., after being directed from the supply reel, to impart the first surface with one or more desired properties, e.g., a hydrophilic material, an antithrombotic material, an antimicrobial material, an anti-hemolytic material, and/or a drug-eluting material.

The coated sleeve may be cut between the first and second ends to create opposing edges extending between the first and second ends, e.g., by creating a longitudinal seam or gap that extends substantially parallel to a longitudinal axis of the sleeve. The cut sleeve may opened by separating the opposing edges, and, if provided on a supply mandrel, the supply mandrel may be removed from within the sleeve. The cut sleeve may then be positioned around an uptake mandrel to reverse the sleeve such that the coated first surface is oriented inwardly towards the uptake mandrel and the opposing edges are disposed adjacent one another.

Optionally, a tubular structure may be attached around the reversed cut sleeve, thereby providing a tubular device comprising an inner surface with the one or more desired properties. For example, a reinforcing layer may be applied around the reversed cut sleeve and uptake mandrel, and the resulting assembly may be wrapped around an uptake reel or other storage device. In this example, the uptake reel may be subsequently introduced into further processes, e.g., to apply one or more additional layers around the reinforcing layer. The resulting tubular device may be cut or otherwise separated into a plurality of individual tubular bodies, e.g., catheter or lead bodies.

In accordance with yet another embodiment, a method is provided for making tubular devices sized for introduction into a body lumen from a thin-walled sheet that includes an outer first surface, an inner second surface, and longitudinal edges extending between first and second ends. The sheet may be secured around a first mandrel such that the longitudinal edges extend along a longitudinal axis of the first mandrel and the first surface is disposed outwardly. In one embodiment, the sheet may be secured around the first mandrel by engaging the sheet along the longitudinal edges with one or more features on the mandrel. For example, the first mandrel may include an elongate slot that extends longitudinally along the first mandrel, and the longitudinal edges of the sheet may be captured in the slot to secure the sheet around the first mandrel. Alternatively, the first mandrel may include ridges or other features that extend longitudinally along the first mandrel, and the longitudinal edges may be placed over the one or more features such that one or more clips may capture the features to engage the longitudinal edges between the one or more clips and features.

A coating may then be applied to the first surface of the sheet that imparts the first surface with one or more desired properties. The coated sheet may then be removed from the first mandrel and reversed to provide a coated liner, which may be incorporated into one or more tubular devices.

For example, the coated sheet may be positioned around a second mandrel (which may be the same or different from the first mandrel) such that the coated first surface is oriented inwardly towards the second mandrel and the longitudinal edges are disposed adjacent one another. One or more layers may then be attached around the coated sheet to provide a catheter component or other tubular device having a coated lumen.

In accordance with still another embodiment, a method is provided for making a tubular device sized for introduction into a body lumen from a thin-walled sleeve that includes an outer first surface and an inner second surface extending between first and second ends of the sleeve. The sleeve may be secured around a mandrel such that the first surface is disposed outwardly, e.g., by engaging one or more clips over one or more mating features on the mandrel to capture the sleeve between the clip(s) and feature(s). The secured sleeve may be coated, and then removed from the mandrel to provide a coated liner, e.g., for storage and/or incorporation into one or more tubular devices.

In accordance with yet another embodiment, a method is provided for making a tubular device sized for introduction into a body lumen using a mandrel including a first end, a second end, and an outer surface extending between the first and second ends. For example, the mandrel may be solid or tubular elongate body or a plate defining the outer surface. A coating material may be applied to the outer surface of the mandrel, e.g., by dipping, spraying, rolling, brushing, and the like, without curing the coating material. A substrate, e.g., a sheet or sleeve, may be positioned over the mandrel such that a first surface of the substrate contacts the coating material on the outer surface of the mandrel. The coating material may be cured through the substrate such that the coating material bonds to the first surface of the substrate to provide a coating having one or more desired properties. The coated substrate may provide a coated liner, which may be incorporated into one or more tubular devices.

In an exemplary embodiment, the coating material may be cured through the substrate. For example, the substrate may be exposed to ultraviolet light and the substrate may be at least partially transparent to the ultraviolet light such that ultraviolet light passes through the substrate to at least partially cure the coating material. In addition or alternatively, inward pressure and/or heat may be applied to the substrate to cure the coating material and/or bond the coating material to the first surface of the substrate.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 8A-8D are cross-sectional views of a coated sheet on a mandrel, such as that shown in FIG. 5B, having a reinforcing layer and an outer jacket provided around them to make a tubular member having a coated lumen.

FIG. 9A-9D are cross-sectional views of a coated sheet on mandrel, such as that shown in FIG. 6C, having a reinforcing layer and an outer jacket provided around them to make a tubular member having a coated lumen.

FIG. 10A-10D are cross-sectional views of a coated sheet on mandrel, such as that shown in FIG. 7F, having a reinforcing layer and an outer jacket provided around them to make a tubular member having a coated lumen.

FIG. 12A is a perspective view of rolls of different liner material being separated into individual sheets to be attached together to form a composite sheet.

FIG. 12B is a side view of the sheets of FIG. 12A, showing a method for attaching ends of the sheets to form a composite sheet.

FIG. 12C is a detail of an alternate method for attaching ends of the sheets of FIG. 12A to form a composite sheet.

FIG. 12D is a perspective view of the composite sheet resulting from the method of FIGS. 12A-12B.

FIGS. 21A-21E show another method for making a liner component having a coating on an interior surface thereof.

FIGS. 28A-28D are side views of an exemplary mandrel and substrate, showing another method for making a coated liner.

FIGS. 29A-29C are side views of another exemplary mandrel and substrate, showing yet another method for making a coated liner.

DETAILED DESCRIPTION OF THE EXEMPLARY EMBODIMENTS

Figure 1A:
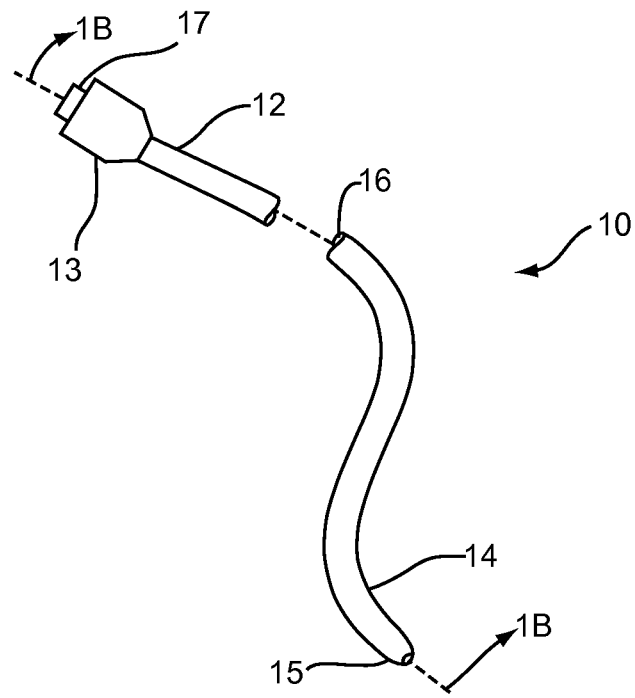
FIG. 1A is a perspective view of an exemplary embodiment of a tubular device, including a lumen extending between proximal and distal ends thereof.
Figure 1B:
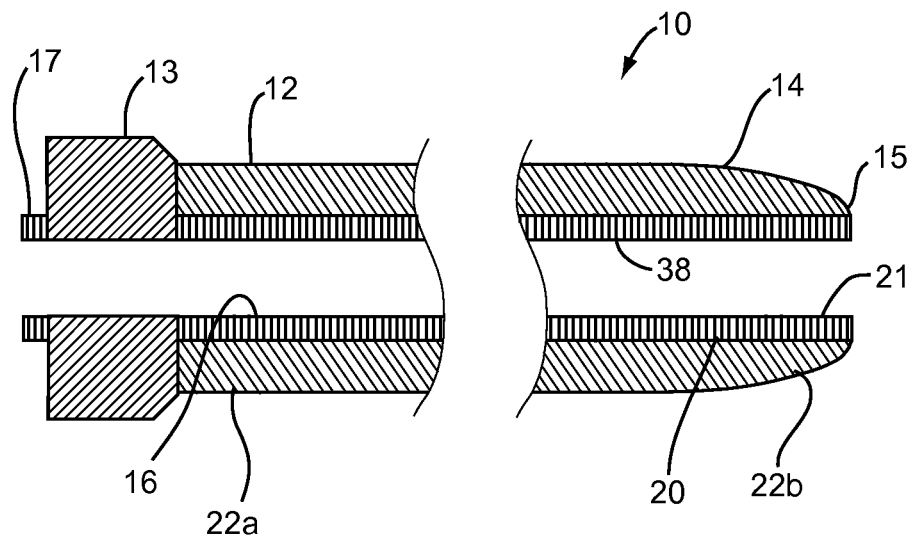
FIG. 1B is a cross-sectional view of the tubular device of FIG. 1A, taken along line 1B-1B, showing a coated liner surrounding the lumen and an outer layer surrounding the coated liner.

Turning to the drawings, FIGS. 1A and 1B show an exemplary embodiment of an apparatus 10 for accessing a body lumen (not shown) and/or for delivering one or more fluids, agents, and/or instruments (also not shown) within a body lumen. In exemplary embodiments, the apparatus 10 may be a guide catheter, a procedure catheter, a sheath, an imaging device, or other tubular device sized for introduction into a body lumen, such as a vessel within a patient's vasculature, a passage within a patient's gastrointestinal tract, urogenital tract, reproductive tract, respiratory tract, lymphatic system, and the like.

Generally, the apparatus 10 is an elongate tubular member including a proximal end 12, a distal end 14 sized for insertion into a body lumen, and a lumen 16 extending between the proximal and distal ends 12, 14. Optionally, the apparatus 10 may include one or more additional lumens (not shown), which may be disposed concentrically around or side-by-side with the lumen 16. The lumen 16 may be sized for receiving a guide wire, procedure catheter, cardiac lead, needle, or other instrument (not shown), and/or for delivering fluids or other flowable agents or materials therethrough.

Optionally, the distal end 14 may include a tapered, rounded, or otherwise shaped distal tip 15, e.g., to provide a substantially atraumatic tip and/or facilitate advancement or navigation through various anatomy. In addition or alternatively, the distal end 14 may include one or more therapeutic and/or diagnostic elements, e.g., one or more balloons, stents, sensors, electrodes, steering mechanisms, imaging devices, helical anchors, needles, and the like (not shown), depending upon the particular intended application for the apparatus 10.

Optionally, the proximal end 12 may include a handle 13 and/or one or more ports, e.g., port 17 communicating with the lumen 16. In addition or alternatively, the handle 13 and/or proximal end 12 may include one or more connectors, such as luer lock connectors, electrical connectors, and the like, for connecting other devices (not shown) to the apparatus 10, such as syringes, displays, controllers, and the like (also not shown). In addition, the handle 13 may include one or more actuators, such as sliders, buttons, switches, and the like, e.g., for activating and/or manipulating components (also not shown) on the distal end 14 or otherwise operating the apparatus 10.

With particular reference to FIG. 1B, the apparatus 10 generally includes an inner liner 20 surrounding the lumen 16 and an outer layer 22 surrounding the inner liner 20. The inner liner 20 may include a relatively thin film, sheet, or other material including an inner surface 21. The inner surface 21 may include a coating 38 having one or more desired properties, e.g., a predetermined lubricity, hydrophilic characteristic, and the like, as described further below.

For example, the liner 20 may be formed from a single layer or multiple layers of material, e.g., having a thickness between about 0.0001-0.050 inch (0.0025-1.25 mm), 0.0001-0.01 inch (0.0025-0.25 mm), 0.0001-0.003 inch (0.0025-0.076 mm), or 0.0001-0.0015 inch (0.0025-0.038 mm). In exemplary embodiments, the liner 20 may be formed from plastics, e.g., thermoplastics, such as polyether block amide ("PEBAX"), urethane, nylon, and the like, fluoropolymers, such as PTFE, FEP, TFE, and the like, thermoset, and thermoform plastics, such as polyimide or polyester, and the like. For example, the liner 20 may be Ether-based or Ester-based polyurethane. However, other suitable polymers may also be used, such as nylon (including nylon 6/6, nylon 11, nylon 12, PEBA) and engineered resins (including Zytel, Rilsan, Grilamid, Vestamid, Pebax), polyethylene, polyvinylchloride, fluoropolymers (including PTFE, FEP, PFA, PVDF, THV, ETFE, ECFE), polyethylene terepthalate polyester, polyolefin, polyetheretherketone, polypropylene, polyolefin, silicone, natural and synthetic rubbers, polystyrene, polycarbonate, polymethylmethacrylate, and the like. Alternatively, the liner 20 may be formed from thin metal sheets, such as stainless steel or Nitinol, or composite materials. Alternatively, the liner 20 may be formed from woven, mesh, or nonwoven materials or fabrics, such as nylon, polyester, Tyvek® (flash-spun high-density polyethylene fiber material), and the like.

The liner 20 may have a substantially homogenous construction, although, alternatively, the construction may vary along the length to provide desired properties, e.g., as described further below with reference to FIGS. 11A and 11B. For example, the durometer of material may vary along the length of the thin film sheet 30. Furthermore, the liner 20 may have one or more transition regions along its length, transitioning from one desired construction to another, including from one desired material to another.

One or more coatings 38 may be applied to the inner surface 21 of the liner 20 during fabrication. In an exemplary embodiment, the coating includes a hydrophilic material, such as Polyvinylpyrrolidone, and may be sprayed or otherwise applied onto the surface 21 during fabrication to apply a substantially uniform thickness coating. However, other suitable hydrophilic materials may also be used, including poly (ethylene oxide), poly(propylene oxide), poly(ethylene glycol), poly(n-vinyl lactam) polyacrylamide, methylcellulose, hydroxypropyl cellulose, hydroxypropylmethyl cellulose, polyacrylic acids, hydroxyethyl methacrylate, polyvinyl alcohols, polyvinyl ethers, hyaluronan, polyurethanes, silicone hydrogel, soy-based hydrogels, and fluorocarbon-sulfone compounds.

The hydrophilic material may provide a predetermined lubricity on the inner surface 21. Alternatively, other materials may be applied to provide one or more desired properties on the inner surface 21 e.g., lubricious, biocompatible, hemocompatible, antithrombotic, procoagulant, antimicrobial, antibiotic, anti-encrustive, pH modulating, growth promoting, growth inhibiting, antiproliferative, endothelialization promoting, cell adhesion promoting, MR signal emitting, radiodense, echogenic, catalytic, immune modulating, anti-hemolytic, drug-eluting, drug delivery, and the like.

Following application of the coating 38 on the inner surface 21, e.g., using any of the apparatus and methods described elsewhere herein, the coating may be cured, cross-linked, or otherwise processed to increase the strength of adhesion of the coating 38 to the surface 21, e.g., using heat, ultraviolet ("UV") light, chemical processing, and the like, as described further below.

The outer layer 22 may be attached to the inner liner 20, e.g., by laminating, adhering, adhesive bonding, ultrasonic welding, reflowing or other heating, and the like, as described elsewhere herein.

Optionally, the outer layer 22 may include one or more sublayers (not shown). For example, the outer layer 22 may include a braided or helical reinforcing layer (not shown) surrounding the inner liner 20 and one or more tubular layers (also not shown) surrounding the reinforcing layer and/or between the reinforcing layer and the inner liner 20. In exemplary embodiments, the reinforcing layer may include one or more round or flat wires, filaments, strands, and the like, e.g., formed from metal, such as stainless steel, plastic, woven fibers, such as glass, Kevlar, and the like, or composite materials. Materials that may be used in the outer layer 22 include doped or undoped PEBAX, urethane, nylon (including nylon 6/6, nylon 11, nylon 12, PEBA) and engineered resins (including Zytel, Rilsan, Grilamid, Vestamid), polyethylene, polyvinylchloride, fluoropolymers (including PTFE, FEP, PFA, PVDF, THV, ETFE, ECFE), polyethylene terepthalate polyester, polyetheretherketone, polypropylene, silicone, natural and synthetic rubbers, polystyrene, polycarbonate, polymethylmethacrylate, and the like. Materials may be primarily selected for optimal mechanical, bonding, and/or other properties and subsequently imparted with desired surface properties, for example lubricity, by coating.

Exemplary outer layers that may be included in the apparatus 10 and methods for making them are disclosed in U.S. Pat. Nos. 4,478,898, 4,863,442, 5,217,440, 5,254,107, 5,676,659, 5,811,043, 5,836,926, 6,004,310, 6,669,886, 6,837,890, and 6,945,970. The entire disclosures of these references are expressly incorporated by reference herein.

The outer layer 22 may have a substantially homogenous construction between the proximal and distal ends 12, 14. Alternatively, the construction may vary along the length of the apparatus 10 to provide desired properties. For example, the outer layer 22a at or adjacent the proximal end 12 may be substantially rigid or semi-rigid, e.g., providing sufficient column strength to allow the apparatus 10 to be pushed from the proximal end 12. In addition, the reinforcing layer or other material in the outer layer 22 may allow the apparatus 10 to be twisted from the proximal end 12, e.g., to rotate the distal end 14 within a patient's body. Thus, the distal end 14 of the apparatus 10 may be manipulated within a patient's body from the proximal end 12 without substantial risk of buckling and/or kinking. Optionally, the outer layer 22b at or adjacent the distal end 14 may be substantially flexible or semi-rigid, e.g., to allow the distal end 14 to bend easily or otherwise be advanced through tortuous anatomy and/or provide a substantially atraumatic distal tip 15. Furthermore, the outer layer 22a, may have one or more transition regions along its length, transitioning from one desired construction to another.

In exemplary embodiments, the apparatus 10 may have an outer diameter between about half and twenty millimeters (0.5-20 mm), and a length between about five and one hundred fifty centimeters (5-150 cm). The inner liner 20 may have a wall thickness between about 0.0001-0.01 inch (0.0025-0.25 mm) and the outer layer 22 may have a wall thickness between about 0.0005-0.2 inch (0.0127-5.08 mm).

Figure 1C:
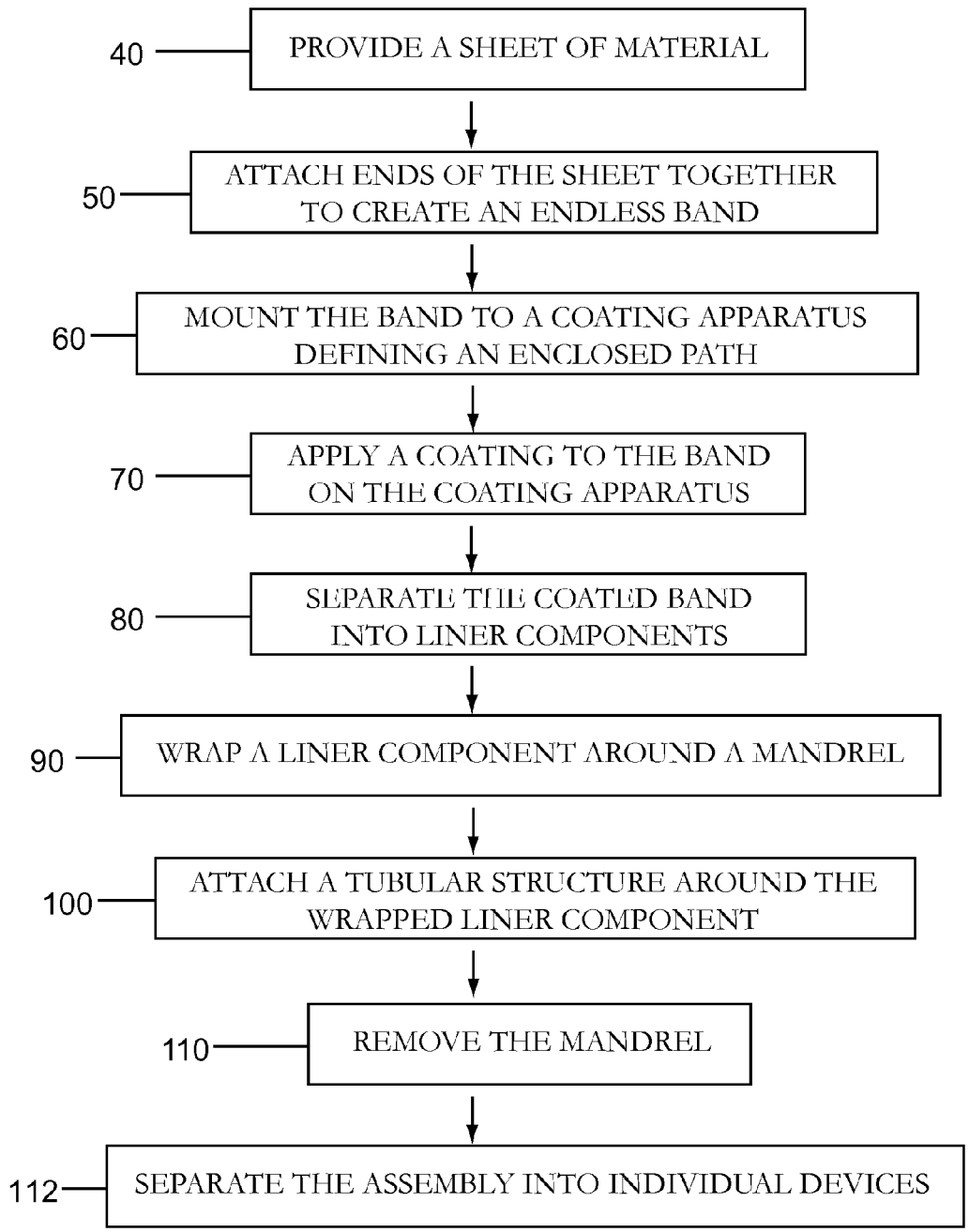
FIG. 1C is a flow chart showing an exemplary method for making tubular devices, such as the tubular device of FIGS. 1A and 1B.
Figure 2A:
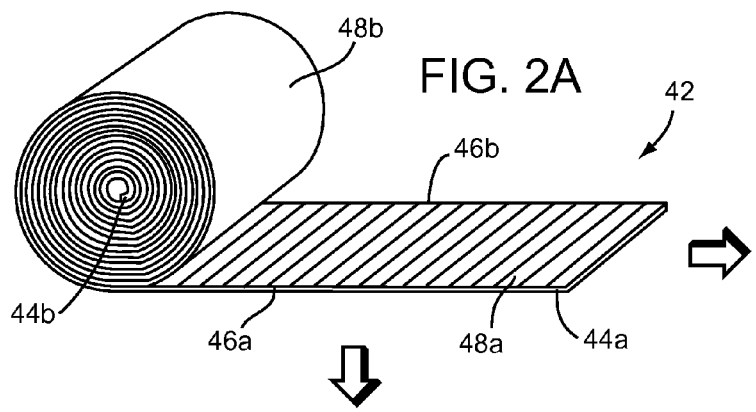
FIGS. 2A and 2B are perspective views of a sheet that may be formed into an endless band that may be used to make one or more liners.
Figure 2B:
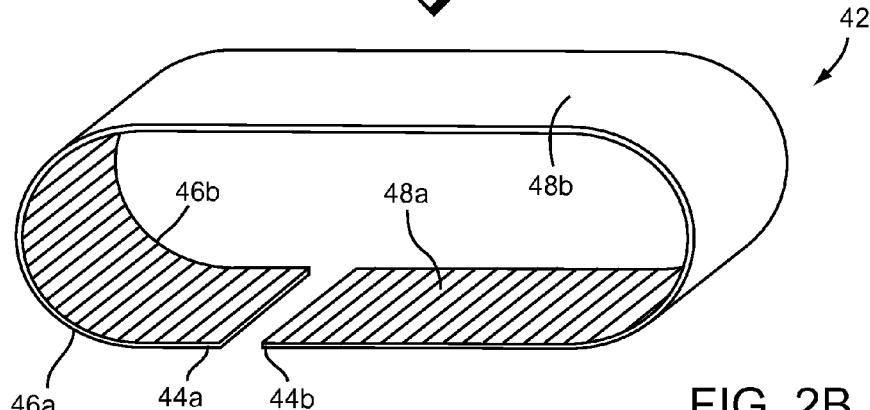

Turning to FIG. 1C, an exemplary method is shown for making one or more tubular devices, such as the apparatus 10 of FIGS. 1A and 1B. Initially, at step 40, a sheet of material may be provided, e.g., that may be used to make the inner liner 20 of the apparatus 10. An exemplary embodiment of a sheet of material 42 is shown in FIGS. 2A and 2B. As shown, the sheet 42 includes first and second ends 44a, 44b, longitudinal edges 46a, 46b extending between the first and second ends 44a, 44b, and first and second surfaces 48a, 48b. In this embodiment, the sheet 42 may include a substantially uniform construction, e.g., being formed from a single material having a substantially uniform thickness and mechanical properties. Alternatively, the material, mechanical properties, thickness, durometer, color, and/or other properties of the sheet 42 may be varied, e.g., along its length between the first and second ends 44a, 44b, as described further below. Properties of the sheet may be varied to impart desirable properties to a tubular device or other apparatus into which the sheet is incorporated as a liner, or may be varied to aid in fabrication. For example, varying color along with other properties may enable easy identification or alignment of transitions and/or identification of coated surfaces during processing or assembly of the sheet.

Returning to FIG. 1C, at step 50, ends of the sheet intended to create one or more liners may be attached together to create an endless band. For example, as shown in FIGS. 2B-2J, the first and second ends 44a, 44b of the exemplary sheet 42 are shown being attached together to create an endless band 52. In this example, the first surface 46a of the sheet 42 defines an inner surface of the band 52 and the second surface 46b defines an outer surface of the band 52.

Figure 2C:
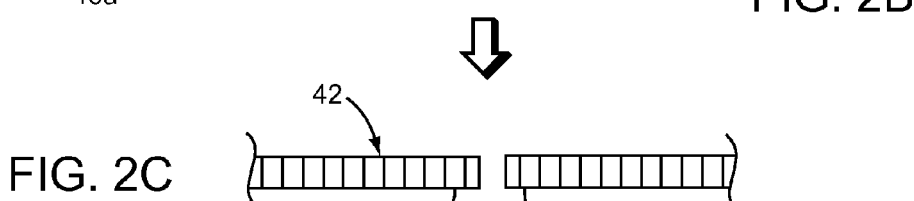
FIGS. 2C and 2D are details showing a method for attaching ends of the sheet of FIGS. 2A and 2B to form an endless band.
Figure 2D:
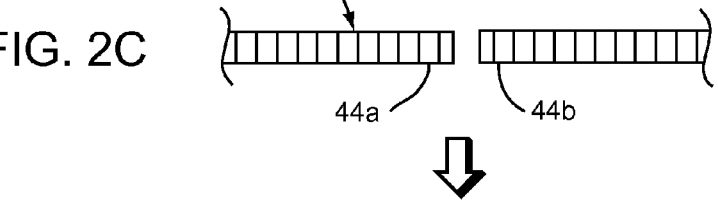
Figure 2E:
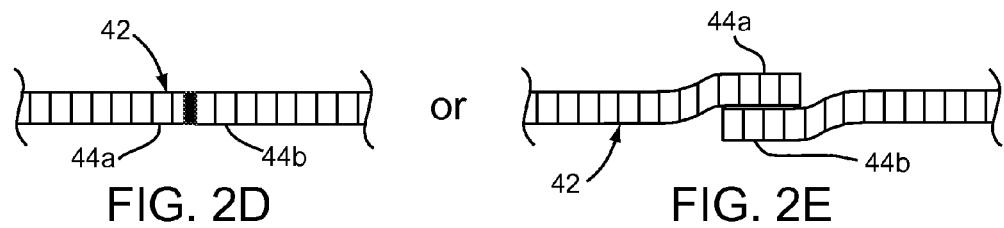
FIG. 2E is a detail showing an alternate method for attaching ends of the sheet of FIGS. 2A and 2B to form an endless band.
Figure 2F:
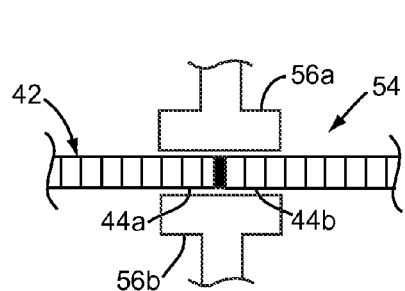
FIGS. 2F-2H are details showing additional alternate methods for attaching ends of the sheet of FIGS. 2A and 2B to form an endless band.
Figure 2G:
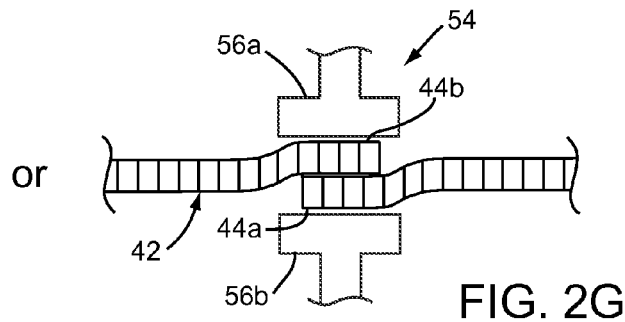
Figure 2H:
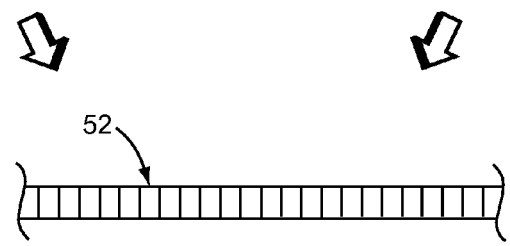
Figure 2I:
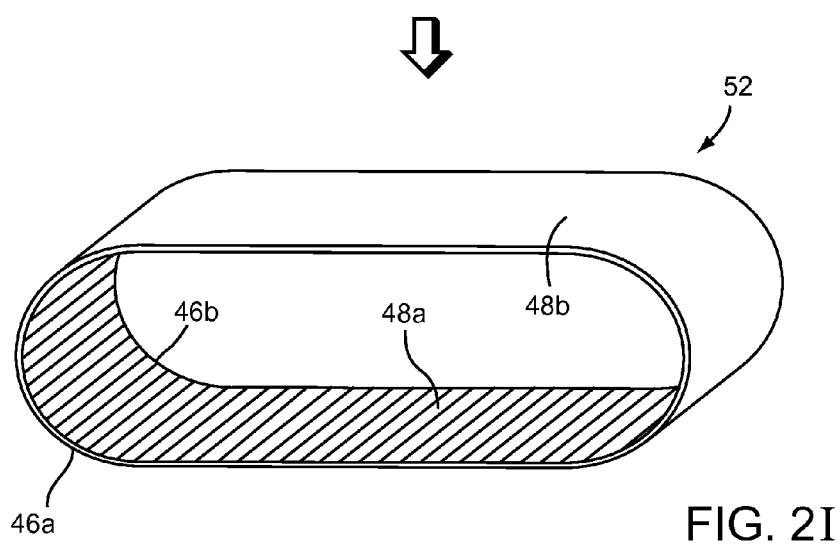
FIGS. 2I and 2J are perspective and side views, respectively, of an exemplary embodiment of an endless band that may be used to make one or more liners.
Figure 2J:
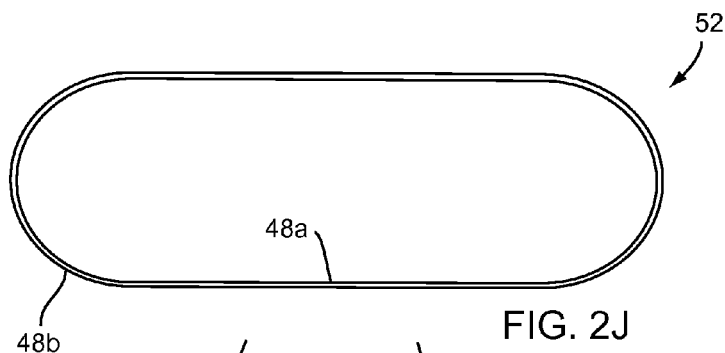

With particular reference to FIGS. 2C and 2D, the first and second ends 44a, 44b may be butted together and attached, for example, by welding (e.g., sonic welding), fusing (e.g., heating, melting, or otherwise reflowing the material), bonding with adhesive, and the like. Alternatively, the ends 44a, 44b may be attached together using one or more fasteners, e.g., staples, clips, threads, tape, and the like (not shown), which may facilitate separating the ends 44a, 44b of the sheet 42 after processing the endless band 52, if desired. FIG. 2F shows an exemplary embodiment of a heating assembly 54 including first and second plates 56a, 56b that may be used to fuse the butted ends 44a, 44b. FIGS. 2E and 2G show an alternative process in which the ends 44a, 44b of the sheet 42 are lapped over one another by a desired distance and attached together, e.g., using the heating assembly 54. In either option, the resulting seam may have a substantially uniform thickness, similar to the rest of the sheet 42 creating the band 52, e.g., as shown in FIGS. 2H-2J. Thus, the resulting band 52 may have a substantially uniform thickness and/or other substantially homogeneous mechanical properties. Alternatively, the thickness of the seam may be greater or otherwise not the same as the rest of the sheet 42, e.g., if the seam is not intended to be used as part of a liner for a tubular device (not shown) or if the seam is reflowed to a similar thickness to the sheet 42 during subsequent processing, e.g., as described elsewhere herein.

Alternatively, an endless band may be created by methods other than attaching together ends of a sheet. For example, an extruded tube (not shown) may be cut in relatively short lengths and stretched, blown, or otherwise expanded to increase its diameter. Alternatively, an endless band may be created from multiple relatively narrower endless bands or one or more strips joined with a helical seam, e.g., as described below.

Returning to FIG. 1C, at step 60, the endless band may be mounted to a coating apparatus, e.g., which may define a substantially enclosed path. Once the endless band is mounted to the coating apparatus, at step 70, one or more coatings may be applied to at least one of the inner surface and the outer surface of the band using the coating apparatus. The coating(s) may be applied to the surface(s) substantially continuously, i.e., by directing the endless band around the enclosed path one or more times. A single pass or circuit is completed when any point on the endless band passes from a starting point along the entire length of the enclosed path and returns to the starting point.

Figure 3A:
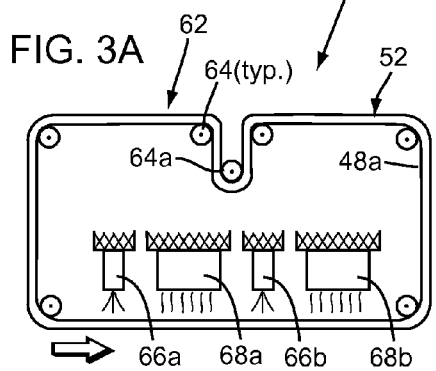
FIG. 3A is a schematic of a first exemplary embodiment of an apparatus showing a process for coating an inner surface of an enclosed band, such as the band of FIGS. 2I and 2J.

For example, FIG. 3A shows an exemplary embodiment of a coating apparatus 62 that includes a roller assembly including a plurality of rollers or pulleys 64 and one or more coating elements 66, 68. The rollers 64 may be spaced apart from one another to define a substantially enclosed path along which the endless band 52 may be mounted and directed. At least one of the rollers 64 may include a motor or other drive mechanism (not shown) for pulling or otherwise directing the endless band 52 along the enclosed path. In addition, one or more of the rollers 64 may be spatially adjustable, for example, movable manually or automatically relative to the other rollers 64, to adjust tension of the endless band 52, e.g., to maintain a desired tension to facilitate directing the endless band 52 along the enclosed path. For example, as shown in FIG. 3A, a tensioning roller 64a may apply tension to the endless band 52 based on its weight or additional added weight (e.g., by gravity), using a spring assembly (not shown), and the like.

The rollers 64 may have a width corresponding to the width of the endless band 52, e.g., between about 0.005 to ninety six inches (0.005-96"), or between about two to twelve inches (2-12"). For example, the width of the rollers 64 may correspond to the circumference of individual liners, to the circumference of multiple liners or to the length of individual liners being formed from the endless band 52. Optionally, the rollers 64 may include sprockets or other features for positively engaging the endless band 52, although alternatively, the material of the rollers 64 may itself allow the endless band 52 to be directed around the rollers 64 with minimal slippage.

Generally, the coating element(s) include one or more applicators 66 for applying one or more coating materials to an inner surface 48a of the endless band 52, and one or more curing devices 68 for curing the coating material. As shown, the coating apparatus 62 includes a first applicator 66a and curing device 68a spaced apart along the enclosed path from a second applicator 66b and curing device 68b. The applicators 66 may apply the same coating material or different materials, e.g., to provide a multiple layer coating on the endless band 52. For example, in one embodiment, the first applicator 66a may apply an initial coating of hydrophilic material, which may facilitate adhesion and/or uniform coverage or a second coating of hydrophilic material applied by the second applicator 66b. In another example, the first applicator 66a may apply a first therapeutic agent (e.g., an anti-proliferative agent) and the second applicator 66b may apply a second therapeutic agent (e.g., an anti-thrombotic agent) over the first therapeutic agent. In still another example, one or more primers may be applied before applying one or more desired coatings. Alternatively, only a single applicator 66 and curing device 68 may be provided (not shown), for example, to provide a single coating layer, e.g., by passing the endless band 52 only once past the applicator 66 and curing device 68, although multiple layers may also be applied in such a configuration by simply directing the endless band 52 around the enclosed path multiple times. In a further alternative, a plurality of applicators 66 may be located before a single curing device 68 (not shown).

In exemplary embodiments, the applicator(s) 66 may include one or more sprayers, rollers, brushes, sponges, dipping assemblies, mayer rods, silk screening devices, spin coating devices, plasma coating devices, vapor deposition devices, and the like, e.g., as appropriate to apply a desired coating material to the endless band 52. The curing device(s) 68 may include one or more heating elements, sources of ultraviolet light, blowers, humidifiers, dryers, and the like, as appropriate to cure the coating material applied before the respective curing device 68. Alternatively, one or more of the curing device(s) 68 may be eliminated, e.g., if the coating material cures automatically.

Figure 3B:
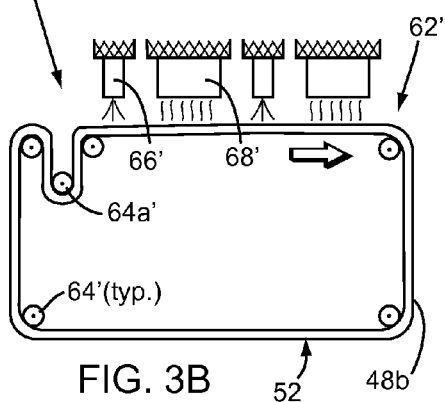
FIG. 3B is a schematic of a second exemplary embodiment of an apparatus showing a process for coating an outer surface of an endless band.

Turning to FIG. 3B, another embodiment of a coating apparatus 62' is shown, which is generally similar to the coating apparatus 62 shown in FIG. 3A, except that the applicators 66' and curing devices 68' are located to apply a coating to an outer surface 48b of the endless band 52. Otherwise, the coating apparatus 62' may include similar components and may function similarly to the coating apparatus 62.

Figure 3C:
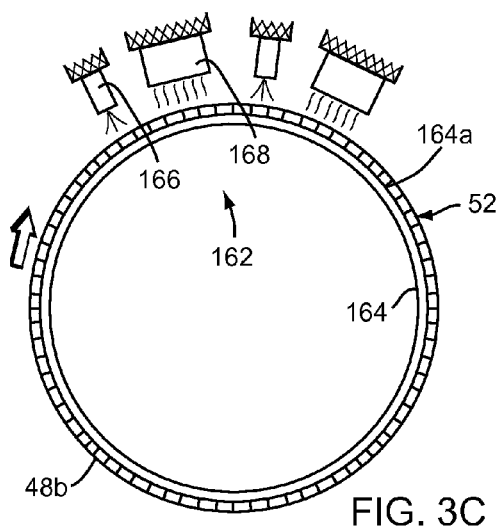
FIG. 3C is a schematic of a third exemplary embodiment of an apparatus showing a process for coating an outer surface of an enclosed band.

Turning to FIG. 3C, still another embodiment of a coating apparatus 162 is shown. Generally, the coating apparatus 162 includes a drum or other rotor 164 including a circumference around which the endless band 52 may be mounted, and one or more coating elements 166, 168 along the enclosed path for applying one or more coating materials to an outer surface 48b of the endless band 52. For example, as shown, the coating elements include two applicators 166 for applying coating material(s) and two curing devices 168, spaced apart from one another adjacent the drum 164, e.g., in first and second sets similar to the coating apparatus 62, although alternatively, only a single applicator 166 and curing device 168 may be provided or multiple applicators and curing devices, as desired (not shown).

In this embodiment, the endless band 52 may be wrapped around an outer surface 164a of the drum 164, which may have a fixed diameter and/or circumference, or may be adjustable to adjust a tension of the endless band 52 wrapped around the drum 164. In addition or alternatively, the endless band 52 may be stretched slightly to mount the endless band 52 around the drum 164, e.g., to secure the endless band 52 around the drum 162 by friction. Optionally, the endless band 52 may be substantially fixed to outer surface 164a of the drum 164 using one or more other features, e.g., a low-tack adhesive, vacuum ports in the drum 164 to pull the endless band 52 against the outer surface 164a, one or more fasteners, e.g., clamps or clips applied along the edges of the endless band 52, studs or other fasteners that penetrate through the material of the endless band 52, magnetic fasteners placed over the endless band 52 that are attracted to the drum 164 material, and the like (not shown).

With the endless band 52 mounted to the drum 162, the drum 162 may be rotated, thereby directing the endless band 52 along an enclosed path corresponding to the circumference of the drum 162. The applicator(s) 166 and curing device(s) 168 may be spaced apart in desired sets or configurations, similar to those described above to apply and cure one or more coating materials to the outer surface 48b of the endless band 52.

Figure 3D:
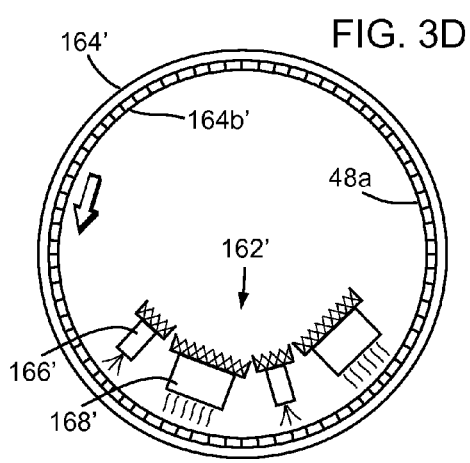
FIG. 3D is a schematic of a fourth exemplary embodiment of an apparatus showing a process for coating an inner surface of an endless band.

Turning to FIG. 3D, yet another embodiment of a coating apparatus 162' is shown that includes a drum 164' and one or more applicators 166' and curing devices 168' similar to the embodiment of FIG. 3C. Unlike the previous embodiment, however, the endless band 52 may be mounted to an inner surface 164b' of the drum 164' rather than an outer surface. In this alternative, fasteners may be needed to removably secure the endless band 52 to the inner surface 164*b*.' Otherwise operation of the coating apparatus 162' may proceed similar to the previous embodiment.

The drums 164, 164' may have a diameter between about twelve and thirty six inches (12-36"), e.g., at least two inches (2") to provide sufficient space to accommodate applicators, curing devices, and/or other components in or around the drums 164, 164' or as large as ten feet (10') in diameter to facilitate large production quantities. The drums 164, 164' may be formed from substantially rigid materials, e.g., a continuous fixed cylinder defining the outer or inner surfaces 164*a*, 164*b*.' Alternatively, the drums 164,164' may include a plurality of plates, each defining a portion of a cylinder, that are arranged adjacent one another to approximate the enclosed path, e.g., with one or more of the plates being movable radially inwardly or outwardly to adjust the circumference of the enclosed path to correspond to the periphery of the endless band being coated and/or otherwise adjust tension of the endless band 52.

Optionally, after any of the coating processes just described, the coated band 52 may be cured or otherwise treated. For example, the coated band may be placed in a chamber and heated, exposed to ultraviolet light, and the like to further cure the coating and/or treat the material of the endless band 52. Alternatively, the endless band 52 may remain on the drum 164, 164' after coating and subjected to subsequent processing. For example, the drum 164, 164' may be removed from a drive axle (not shown) of the coating assembly 162, 162' and moved to another axle or device (not shown), e.g., for additional curing or processing. If desired, the subsequent axle or device may be in an environmental chamber to subject the endless 52 band to desired environmental conditions, e.g., heat, pressure, and/or humidity, compared to those used during the initial coating process. In an exemplary embodiment, a coating may be applied and partially cured using the coating assembly 162, 162' and the drum 164, 164' and coated band may be transferred to an oven (not shown) for additional curing.

Figure 4A:
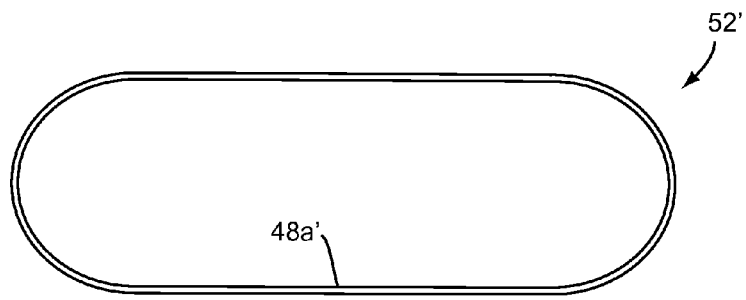
FIGS. 4A and 4B show an exemplary embodiment of an endless band being separated into one or more strips having a coated surface.
Figure 4B:
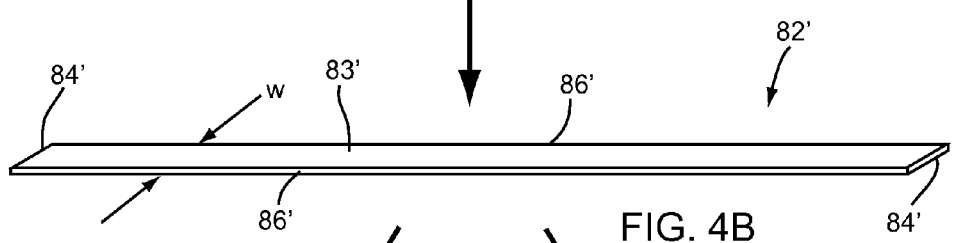

Returning to FIG. 1C, at step 80, the endless band 52 may be separated into one or more liner components. For example, in FIG. 4A, an endless band 52' is shown that has a width corresponding to a circumference of a desired liner. The band 52' may be cut, e.g., between its longitudinal edges to provide a relatively long, narrow strip 82,' as shown in FIG. 4B. Alternatively, the band 52' may have a width greater than individual liners, and may be cut into multiple narrow strips, as described further elsewhere herein.

Figure 7A:
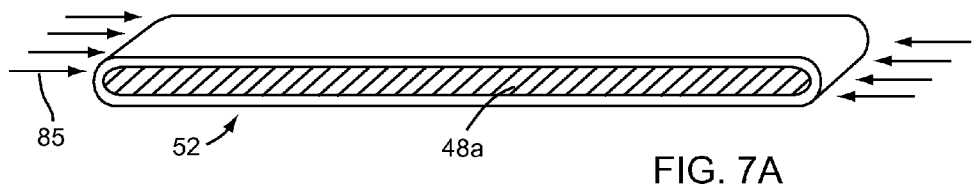
FIGS. 7A and 7B are perspective and side views, respectively, of an endless band having a coated surface being separated into a plurality of narrower endless bands.
Figure 7B:
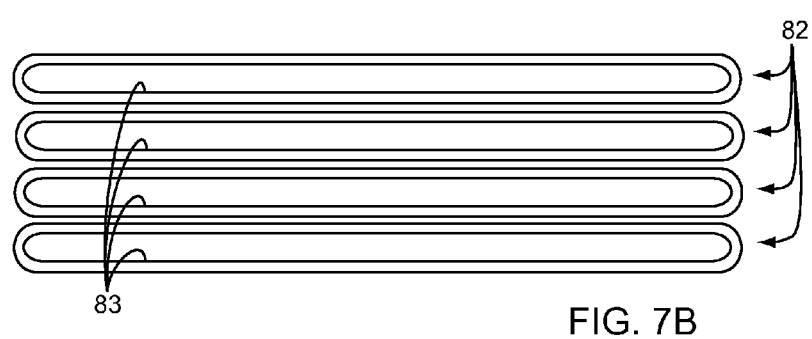

Alternatively, as shown in FIG. 7A, an endless band 52 having a width that is substantially greater than the circumference of a desired liner may be separated into a plurality of relatively narrower bands 82, as shown in FIG. 7B. For example, the endless band 52 may be cut using a plurality of cutting elements 85, shown schematically in FIG. 7A. The cutting elements may include a plurality of blades, wires, lasers, or other cutters capable of cutting through the material of the endless band 52. In one embodiment, the endless band 52 may be folded substantially flat, as shown in FIG. 7A, and directed past an array of cutting elements 85 that substantially simultaneously cut the endless band 52 into the narrower bands 82. Alternatively, narrower bands 82 may be cut from the endless band 52 sequentially using a single cutting element (not shown).

Figure 16A:
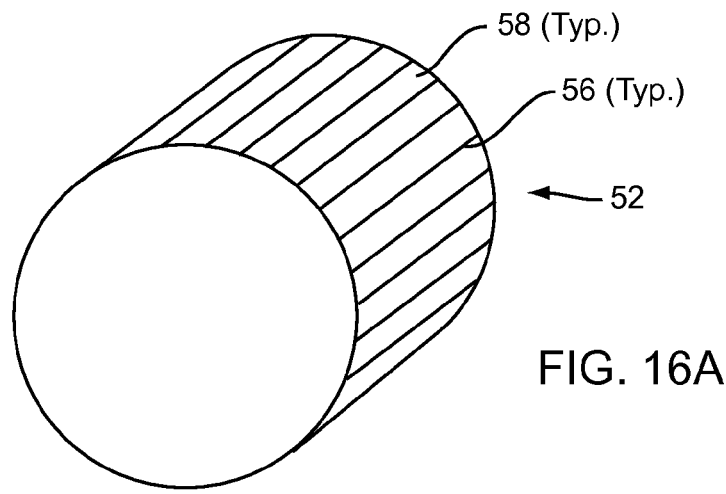
FIG. 16A is a perspective view of a coated endless band, showing axial cut lines for separating the endless band into a plurality of strips.
Figure 16B:
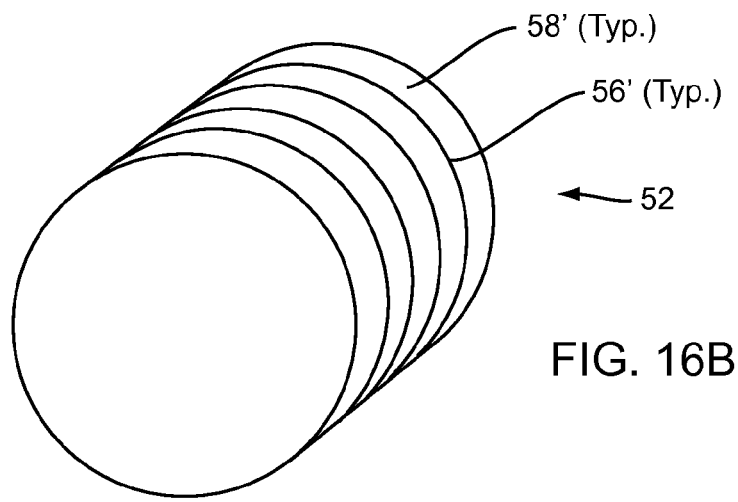
FIG. 16B is a perspective view of a coated endless band, showing circumferential cut lines for separating the endless band into a plurality of narrower endless bands.
Figure 16C:
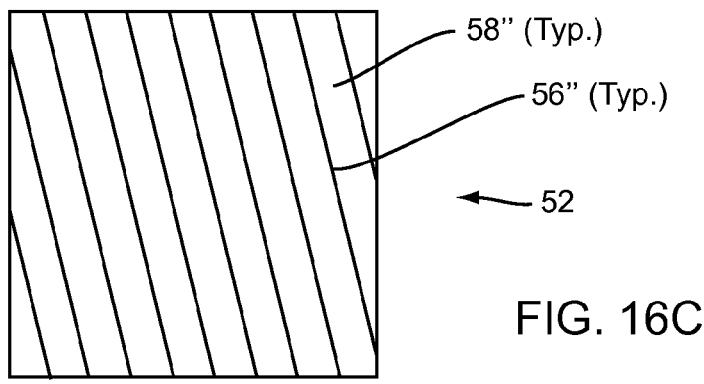
FIG. 16C is a perspective view of a coated endless band, showing a helical cut line for separating the endless band into a single continuous strip.

Turning to FIGS. 16A-16C, the endless band 52 may be separated into liner components in different configurations. For example, as shown in FIG. 16A, an endless band 52 may be cut or otherwise separated along axial cut lines 56 to create multiple strips 58. In this embodiment, the width of the endless band 52 corresponds to the lengths of the strips 58, e.g., which may correspond to the length of one or more liners being formed from the strips 58.

Alternatively, in FIG. 16B, the endless band 52 may be cut or otherwise separated along circumferential cut lines 56' to create multiple relatively narrow bands 58.' In a further alternative shown in FIG. 16C, the endless band 52 may be cut or otherwise separated along a helical cut line 56" to create a single continuous strip 58." Such a continuous strip 58" may be useful for making a plurality of tubular devices using a substantially continuous process, as described elsewhere herein. Alternatively, these processes may be reversed to create an endless band from two or more relatively narrower endless bands or one or more strips. For example, one or more circumferential seams (not shown) may be created between two or more relatively narrow bands 58' to create an endless band 52. Alternatively, a helical seam (not shown) may be created between one or more strips 58" to create an endless band 52. An endless band 52 created in this manner may be further coated, separated into liner components, or otherwise processed as described elsewhere herein.

In yet another alternative, one or more endless bands 52 may be cut or otherwise separated into one or more sheets, such as those depicted in FIG. 12A, and subsequently joined to form a single composite sheet 152 such as that shown in FIG. 12D having different properties along its length, as described further below. The sheet 152 may then be further separated into one or more liner components, also as described further below.

Returning to FIG. 1C, at step 90, one or more liner components created from the endless band may be formed into one or more liners and/or tubular devices. Generally, this involves wrapping each liner component around a mandrel, e.g., such that the coating is disposed inwardly towards the mandrel. Thereafter, at step 100, a tubular structure may be attached around the wrapped liner component and mandrel, e.g., to provide one or more tubular devices, such as the tubular device 10 shown in FIGS. 1A and 1B.

For example, turning to FIG. 4A-5B, an exemplary method for creating a coated liner is shown. As explained above, FIG. 4A shows an exemplary embodiment of an endless band 52' including a coated surface 48*a*' and FIG. 4B shows the endless band 52' cut to provide an elongated strip 82' including a coated surface 83.' The endless band 52' may have been formed and coated using any of the processes described above, or may have been created by separating a wider endless band (not shown) into a plurality of bands similar to band 52.' For example, a relatively wide endless band may be cut to provide a coated sheet, and then the sheet may be cut into individual strips, similar to strip 82.' For example, the coated sheet may be directed through an array of cutters, e.g., blades or wires, laser devices, and the like (not shown), that simultaneously creates a plurality of strips from the coated sheet.

Figure 5A:
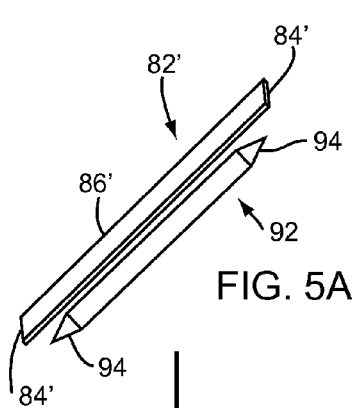
FIGS. 5A and 5B are perspective and cross-sectional views, respectively, of a strip from the band of FIGS. 4A and 4B being wrapped around a mandrel in a longitudinal configuration with the coated surface oriented inwardly towards the mandrel.
Figure 5B:
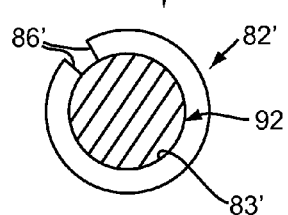

With additional reference to FIGS. 5A and 5B, the strip 82' may have a width "w" corresponding to a circumference of a liner to be formed using the strip 82'. More particularly, the width "w" of the strip may be substantially the same as the circumference of a mandrel 92. The strip 82' may have a length equal to or greater than a length of the mandrel 92 such that ends 84' of the strip 82' may be disposed adjacent respective ends 94 of the mandrel 92, e.g., such that longitudinal edges 86' of the strip 82' extend axially, e.g., substantially parallel to a longitudinal axis of the mandrel 92. As best seen in FIG. 5B, the strip 82 may then be wrapped around the mandrel 92 until the longitudinal edges 86' are disposed adjacent one another. For example, as shown in FIG. 5B, the inner most corners of the longitudinal edges 86' may contact one another or may be spaced slightly apart from one another (not shown), while the outer most corners of the longitudinal edges 86' are spaced apart from one another. Thus, the strip 82' may be wrapped around the mandrel 92 without the longitudinal edges 86 overlapping. Alternatively, the width "w" of the strip 82' may be slightly smaller than the circumference of the mandrel 92 such that a narrow gap (not shown) remains between the longitudinal edges 86' after wrapping the strip 82' around the mandrel 92. Alternatively, the longitudinal edges 86' may be modified such that any gap does not define a substantially straight line between the ends 84' of the strip 82.' For example longitudinal edges 86' may be cut in a sine-wave or zigzag pattern (not shown) such that one edge mirrors the other when the strip 82' is positioned around the mandrel 92.

Optionally, the ends 84' of the strip 82' may be secured relative to the mandrel 92. For example, in one embodiment, the ends 94 of the mandrel 92 may be pointed, and the ends 84' of the strip 82' may be hooked at least partially around the ends 94 of the mandrel 92, e.g., stretching the strip 82' to apply a slight tension along the length of the strip 82' between the ends 84.' Such tension may enhance maintaining the strip 82' wrapped around the mandrel 92 and/or aligning the longitudinal edges 86' along the mandrel 92.

Turning to FIGS. 8A-8D, the strip 82' wrapped around the mandrel 92 may be used to make a tubular device 102, which may be similar to tubular device 10 shown in FIGS. 1A and 1B. For example, as shown in FIGS. 8A-8C, a reinforcing layer 104 and an outer layer 106 may be placed around the strip 82,' e.g., surrounded by a section of heatshrink tubing 108. The entire assembly may be heated to reflow the outer layer 106, e.g., which may flow inwardly through the reinforcing layer and bond to the strip 82', filling any gap between the longitudinal edges 86' of the strip 82.' Exemplary methods for making tubular devices including reinforcing layers and outer layers are disclosed in U.S. Pat. Nos. 7,550,053 and 7,553,387, the entire disclosures of which are expressly incorporated by reference herein.

Returning to FIG. 1C, once the tubular device 102 of FIGS. 8C and 8D is made, at step 110, the mandrel 92 may be removed, along with the heatshrink tubing 108. The resulting tubular device 102 thus includes a lumen 103 surrounded by a coated liner defined by strip 82.' If the tubular device 102 has a length greater than a desired catheter or other finished device, the tubular device 102 may be separated into one or more devices at step 112. This may simply involve cutting the tubular device 102 into desired lengths, or any desired additional features desired for the finished device, such as those described above, may be added to the individual tubular devices 102, e.g., a relatively soft distal tip, a handle, a valve, a shape-set to the distal end, an outer diameter coating, one or more radiopaque markers, and the like (not shown).

Alternatively, the tubular device 102 may be made using a substantially continuous process. For example, if the endless band 52' in FIG. 4A is sufficiently long, the resulting strip 82' shown in FIG. 5A may be wound onto a reel and the like (not shown). The wound strip and reel may then be mounted on a spindle or other feature of an automated apparatus capable of feeding the strip along with other components of the tubular device 102 substantially continuously. Thus, the strip 82' may be used to make a sufficiently long tubular device 102 that may be separated into as few as one or as many as hundreds or thousands of tubular bodies, e.g., by substantially simultaneously feeding components of the tubular bodies from sources, such as reels, through the apparatus until the sources are depleted, whereupon new source(s) may be loaded onto the apparatus and the process continued. Thus, the apparatus and methods described herein may be used to make relatively long tubular bodies, e.g., that are substantially longer than finished catheters or other tubular devices. Exemplary apparatus and methods for such substantially continuous fabrication are disclosed in U.S. Publication No. 2009/0126862, published May 21, 2009, the entire disclosure of which is expressly incorporated by reference herein.

Figure 6A:
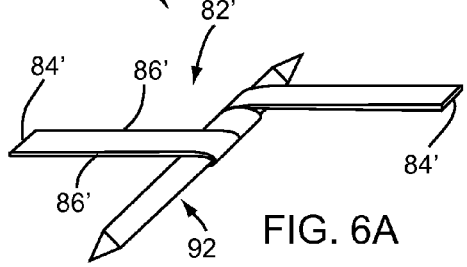
FIGS. 6A and 6B are perspective views and FIG. 6C is a cross-sectional view of a strip from the band of FIGS. 4A and 4B being wrapped around a mandrel in a helical configuration with the coated surface oriented inwardly towards the mandrel.
Figures 6B, 6C:
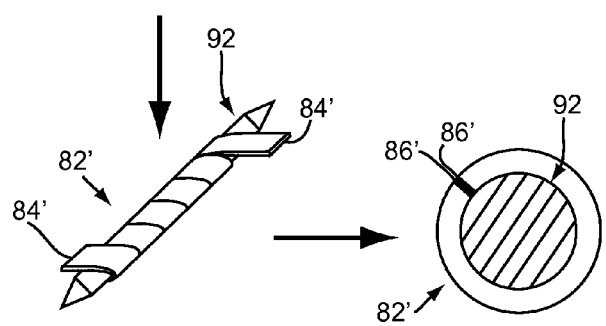

Returning to FIGS. 4A and 4B, with additional reference to FIGS. 6A-6C, another method is shown for creating a liner component. Similar to the method of FIGS. 5A and 5B, a strip 82' may be provided from an endless band 52' (shown in FIGS. 4A and 4B). Rather than wrap the strip 82' around a mandrel 92 in a longitudinal configuration, the strip 82' may be wound helically around a mandrel 92, as shown in FIGS. 6A and 6B. In this embodiment, the width "w" of the strip 82' may not bear any particular relationship to the size of the mandrel 92, other than being narrower than the length of the mandrel 92 such that the strip 82' is wrapped one or more times around the mandrel 92. For example, the strip 82' may be wound around the mandrel 92 with a single rotation of three hundred sixty degrees (360°) or less, e.g., between one half and one full rotation, or may be wound multiple times around the mandrel 92. The strip 82' may be wound such that the longitudinal edges 86' of the strip 82' are disposed adjacent one another along adjacent windings without overlap. The edges 86' may contact one another, e.g., butt up against one another, as shown in FIG. 6C, or may be spaced slightly apart, if desired (not shown). Alternatively, the longitudinal edges 86' may overlap one another (not shown), and the material of the strip 86' may be reflowed during subsequent processing to provide a substantially uniform thickness wall liner, if desired. Optionally, the helically wound strip 82' (or any of the other strips described herein) may include a composite coated liner, e.g., as described elsewhere herein.

As shown in FIGS. 9A-9D, the helically wound strip 82' may be incorporated into a tubular device 102,' e.g., including a reinforcing layer 104 and an outer layer 106, similar to the embodiment of FIGS. 8A-8D. The resulting tubular device 102' may include a coated lumen 103' similar to the tubular device 102, except that the seam from the strip 82' extends helically down the length of the tubular device 102' rather than axially as in the device 102.

Turning to FIGS. 7A-7F, another embodiment of a method for making liner components is disclosed. As explained above, an endless band 52 may be created that includes a coating on at least one of the inner and outer surfaces, e.g., inner surface 48a. The endless band 52 may be cut or otherwise separated into a plurality of narrower endless bands 82, as shown in FIG. 7B. For example, as shown in FIG. 7A, an array of cutters 85 may be provided that are spaced apart from one another by a distance corresponding to the desired width of each of the narrower endless bands 82, as described elsewhere herein. Alternatively, the narrower endless bands 82 may be formed sequentially by passing the endless band 52 multiple times through a cutting device (not shown) that creates one or more narrower endless bands 82 at a time.

Figure 7C:
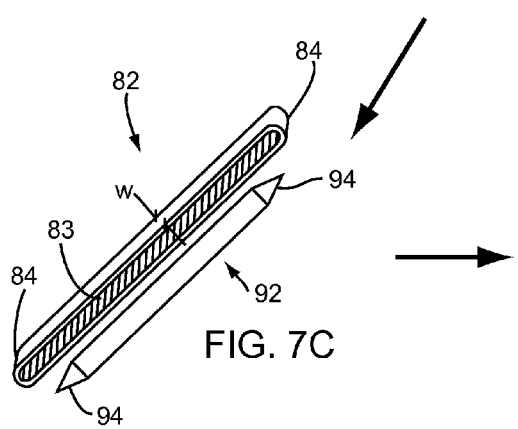
FIGS. 7C and 7D are perspective views of a narrow band being disposed around a mandrel.
Figure 7D:
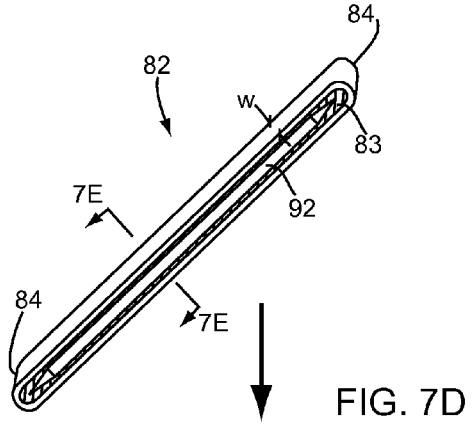
Figure 7F:
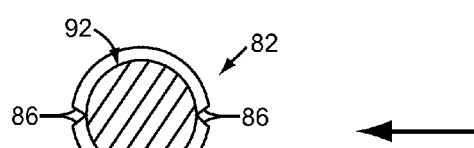
FIGS. 7E and 7F are cross-sectional details of the narrow band and mandrel of FIGS. 7C and 7D, showing the narrow band being disposed around the mandrel.
Figure 7E:
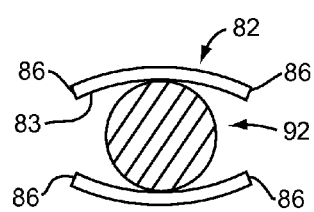

Each narrower endless band 82 may be wrapped around a mandrel 92 with the coated surface 83 oriented inwardly towards the mandrel 92. For example, as shown in FIGS. 7C and 7D, the narrower endless band 82 may be flattened and ends 84 of the band 82 may be received over respective ends 94 of the mandrel 92. The length of the flattened band 82 and the mandrel 92 may be such that the band 82 may be stretched slightly to receive the ends 84 over the ends 94 of the mandrel 92, e.g., to apply a slight tension along the length of the band 82. As shown in FIGS. 7E and 7F, the band 82 may wrap around the mandrel 92 such that longitudinal edges 86 of the band 82 are disposed adjacent one another and extend substantially axially between the ends 94 of the mandrel 92. Alternatively, if desired, the ends 84 of the band 82 may be rotated about the longitudinal axis of the mandrel 92 relative to one another, e.g., such that the longitudinal edges 86 of the band 82 extend helically between the ends 94 of the mandrel 92 (not shown).

Each narrower endless band 82 may have a width having a desired relationship with a circumference of a liner to be formed using the narrower endless band 82. More particularly, the width of the narrower endless band 82 may be substantially half or slightly less than half the circumference of mandrel 92. Thus, as shown in FIG. 7F, the inner most corners of the longitudinal edges 86 may contact one another or may be spaced slightly apart from one another (not shown), while the outer most corners of the longitudinal edges 86 are spaced apart from one another. Thus, the narrower endless band 82 may be wrapped around the mandrel 92 without the longitudinal edges 86 overlapping.

Alternatively, the width "w" of the narrower endless band 82 may be slightly smaller than half the circumference of the mandrel 92 such that a narrow gap (not shown) remains between the longitudinal edges 86 after wrapping the narrower endless band 82 around the mandrel 92. Such a gap may reduce the likelihood of the edges 86 of the narrower endless band 82 shifting and overlapping. In a further alternative, the longitudinal edges 86 may overlap, and the material of the band 86 may be reflowed during subsequent processing to provide a substantially uniform thickness wall liner, if desired (not shown).

Alternatively, multiple narrower endless bands (not shown) may be wrapped around the mandrel 92. The width "w" of each narrower endless band may be substantially equal to c/2n, where "c" is the circumference of the mandrel 92 and n is the number of narrower endless bands used. Alternatively, the width "w" of each of the multiple narrower endless bands (not shown) may be greater than or less than c/2n, resulting in overlaps or narrow gaps, respectively, similar to other embodiments described elsewhere herein.

Optionally, the ends 84 of the narrower endless band 82 may be rotated relative to one another, e.g., to wind the band 82 helically around the mandrel 92. In this option, the longitudinal edges 86 may provide a gap, may be butted together, or may be spaced apart, similar to other embodiments described elsewhere herein.

Turning to FIGS. 10A-10D, the narrower endless band 82, wrapped around the mandrel 92, may be incorporated into a tubular device 102," e.g., including a reinforcing layer 104 and an outer layer 106, similar to the embodiments of FIGS. 8A-9D. Optionally, after applying a reinforcing layer 104 and/or outer layer 106 around the narrower endless band 82 wrapped around the mandrel 92, the ends of the tubular device 102" may be trimmed or otherwise cut to length (not shown), as desired. The resulting tubular device 102" may include a coated lumen 103" similar to the tubular devices 102, 102,' except that the band 82 creates a pair of longitudinal seams that extend down the length of the tubular device 102." The longitudinal seams may extend axially or helically depending upon whether the ends 84 of the band 82 are rotated relative to one another or not.

Figure 11A:
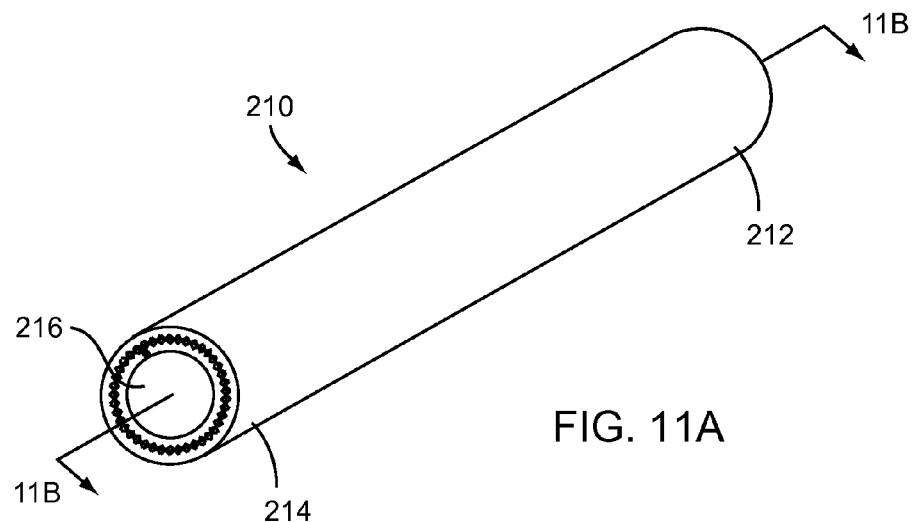
FIG. 11A is a perspective view of another exemplary embodiment of a tubular device, including a lumen extending between proximal and distal ends thereof.
Figure 11B:
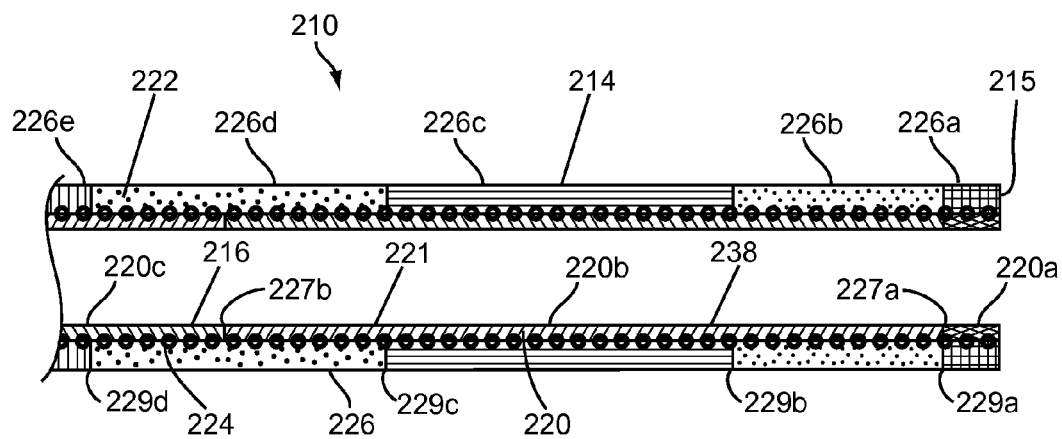
FIG. 11B is a cross-sectional view of the tubular device of FIG. 11A, taken along line 11B-11B, showing a coated liner surrounding the lumen having variable properties along a length of the tubular device.

Turning now to FIGS. 11A and 11B, another embodiment of a tubular device 210 is shown that may be made using the apparatus and methods described herein. Generally, the tubular device 210 is an elongate tubular member including a proximal end 212, a distal end 214 sized for insertion into a body lumen, and a lumen 216 extending between the proximal and distal ends 212, 214. The distal end 214 may terminate in a relatively soft and/or substantially atraumatic distal tip 215, as described further below. Optionally, the apparatus 210 may include one or more additional lumens, a handle and/or one or more ports, or other elements (not shown), similar to other embodiments described herein.

With particular reference to FIG. 11B, the apparatus 210 generally includes an inner liner 220 surrounding the lumen 216 and an outer layer 222 surrounding the inner liner 220, e.g., including a reinforcing layer 224 and an outer tubular layer 226. Similar to the previous embodiments, the inner liner 220 may include a relatively thin film, sheet, or other material including an inner surface 221, and the inner surface 221 may include a coating 238 having one or more desired properties, e.g., a hydrophilic coating.

Unlike the previous embodiments, the inner liner 220 may have a composite construction, e.g., formed from one or more sections of material 220a-220c having different properties than one another. In addition, the outer tubular layer 226 may also be formed from one or more sections of material 226a-226e, also having different properties than one another. Optionally, one or more of the seams 227a, 227b between the adjacent sections 220a-220c of the inner liner 220 may be offset axially from one or more of the seams 229a-229d between adjacent sections 226a-226e of the outer tubular layer 226.

For example, as shown in FIG. 1B, the distal tip 215 of the tubular device 210 may include a relatively soft material for both the outer tubular layer 226 and the inner liner 220, and the reinforcing layer 224 may terminate before the distal tip 215. In an exemplary embodiment, the inner liner 220 may include a distal-most section 220a formed from a relatively soft material, e.g., forty Durometer (40 D) polyurethane, and a distal-most section 226a of the outer tubular layer 226 may be formed from a relatively soft material, e.g., a thirty five Durometer (35 D) PEBAX, which optionally may be doped with Tungsten or Barium.

The distal tip 215 including sections 220a, 226a may be formed separately from the rest of the tubular device 210, e.g., using a lay-up process in which a tube (corresponding to section 226a of the outer tubular layer 226) may be lined with a thin sheet (corresponding to section 220a of the inner liner 220) and then separated into multiple lengths that provide tips for multiple devices. Additional information on methods for making such tips are disclosed in the applications incorporated by reference elsewhere herein.

Adjacent the distal tip 215, the inner liner 220 may include a transition section 220b, e.g., formed from fifty five Durometer (55 D) polyurethane or other material more rigid than the distal-most section 220a, and then a shaft section 220c, e.g., formed from seventy two Durometer (72 D) PEBAX or other material more rigid than the more distal transition section 220b, which may extend from the distal end 214 of the tubular device 210 to the proximal end 212. Similarly, the outer tubular layer 226 may include one or more transition sections 226b-226d (three shown) and a shaft section 226e, which may extend proximally towards the proximal end 212 of the tubular device 210. In the embodiment shown, the seams 229-229d of the outer tubular layer 226 are offset axially or staggered from the seam 227b of the inner liner 220, which may provide smoother stiffness transitions along the length of the distal end 214. Such smoother transitions may reduce the risk of the distal end 214 buckling or kinking, e.g., when the tubular device 210 is directed through tortuous anatomy.

In an exemplary embodiment, the transition sections 226b-226d of the outer tubular liner 226 may be formed from progressively more rigid material in sections away from the distal tip 215. For example, the first transition section 226b may be formed from forty Durometer (40 D) PEBAX, which optionally may be doped similar to the distal-most section 226a, the second transition section 226c may be formed from fifty five Durometer (55 D) PEBAX, and the third transition section 226d may be formed from sixty three Durometer (63 D) PEBAX. The shaft section 226e may be formed from nylon or Pebax, or other material, similar to the exemplary embodiments described elsewhere herein.

The tubular device 210 may be incorporated into a variety of catheters, sheaths, or other medical devices. In an exemplary embodiment, the tubular device 210 may be incorporated into a catheter for delivering cardiac leads into a patient's heart (not shown). In such an example, the tubular device 210 may have a length between about thirty and sixty five centimeters (30-65 cm), and an outer diameter between about four and ten French (4-10 Fr). The proximal end 212 of the tubular device 210 may include a handle or hub (not shown), which may include a port communicating with the lumen 216, e.g., including a hemostatic valve (also not shown), which may provide a substantially fluid-tight seal, while accommodating insertion of leads or other instruments or fluids into the lumen 216. Optionally, the distal end 214 of the tubular device 210 may be shape set in a desired configuration, e.g., biased to a simple or complex curved shape, e.g., as disclosed in the applications incorporated by reference elsewhere herein.

Figure 12E:
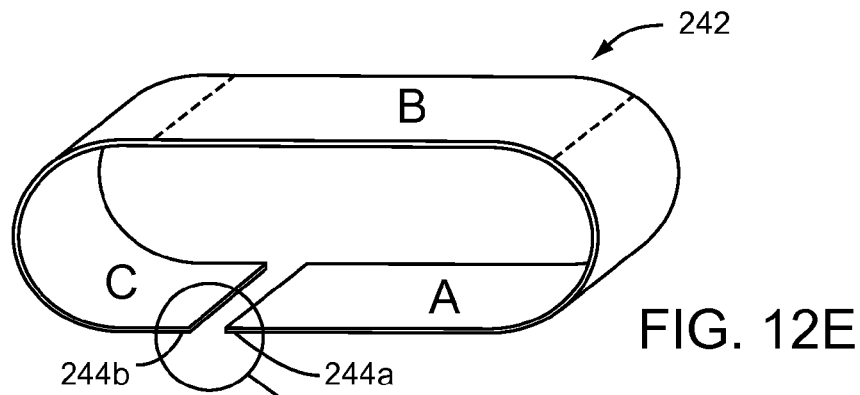
FIGS. 12E and 12F are perspective views of the composite sheet of FIG. 12D being rolled and having its ends attached together.

Turning to FIGS. 12A-12H, an exemplary method is shown for making composite coated liners for tubular devices, such as tubular device 210. As shown in FIG. 12A, a plurality of different materials may be provided, e.g., material A, material B, and material C, which may be cut into sheets that may be attached together to provide a composite sheet 242, as shown in FIG. 12D. For example, materials A, B, C may be cut or otherwise separated into individual sheets 242a, 242b, 242c having desired lengths, e.g., corresponding to the length of respective sections of one or more liners to be formed from the composite sheet 242. The sheets 242a, 242b, 242c may have widths corresponding to the width of an individual liner component or to multiple liner components, similar to the previous embodiments.

Adjacent edges of the sheets 242a, 242b, 242c may be attached together at seams 243a, 243b. For example, as shown in FIG. 12B, one or more heating assemblies 254 may be provided for simultaneously or sequentially fusing butted edges of the sheets 242a, 242b, 242c. Alternatively, as shown in FIG. 12C, edges of the sheets 242a, 242b, 242c may be lapped over one another by a desired distance and attached together, e.g., using the heating assembly 254. In either option, the resulting seams 243a, 243b may have a substantially uniform thickness, similar to the rest of the sheets 242a, 242b, 242c. Thus, the resulting composite sheet 242 may have a substantially uniform thickness and/or other substantially homogeneous mechanical properties. Alternatively, the thickness of the seams 243a, 243b may be greater or otherwise not the same as the rest of the composite sheet 242, e.g., if the seams 243a, 243b are reflowed during subsequent processing, similar to previous embodiments.

Figure 12G:
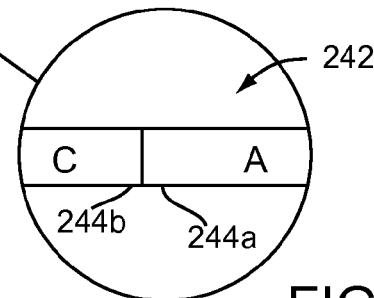
FIG. 12G is a detail showing the ends of the composite sheet of FIGS. 12E and 12F attached together to provide an endless band.
Figure 12H:
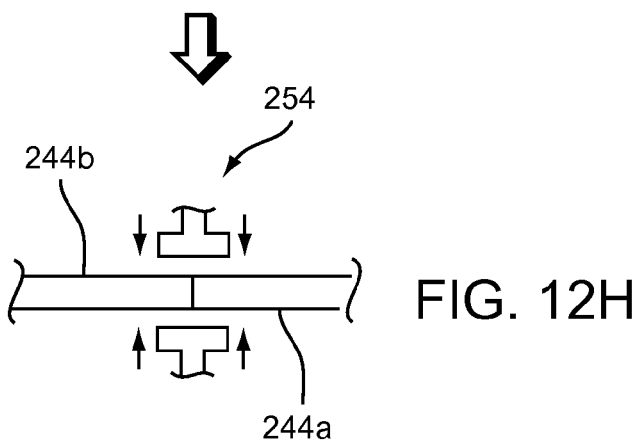
FIG. 12H is a detail showing a method for attaching the ends of the composite sheet of FIGS. 12E and 12F together to form a composite band in preparation for coating a surface of the composite sheet.

Turning to FIGS. 12E-12H, the composite sheet 242 may then be formed into an endless band 252, similar to the previous embodiments. As shown in FIGS. 12G and 12H, ends 244a, 244b of the composite sheet 242 may be attached together, e.g., using heating assembly 254. For example, the ends 244a, 244b may be butted together and attached, for example, by welding (e.g., sonic welding), fusing (e.g., heating, melting, or otherwise reflowing the material), bonding with adhesive, and the like. Alternatively, the ends 244a, 244b may be attached together using one or more fasteners (not shown), similar to previous embodiments, which may facilitate separating the ends 244a, 244b of the composite sheet 242 after processing the endless band 252, if desired.

Figure 15A:
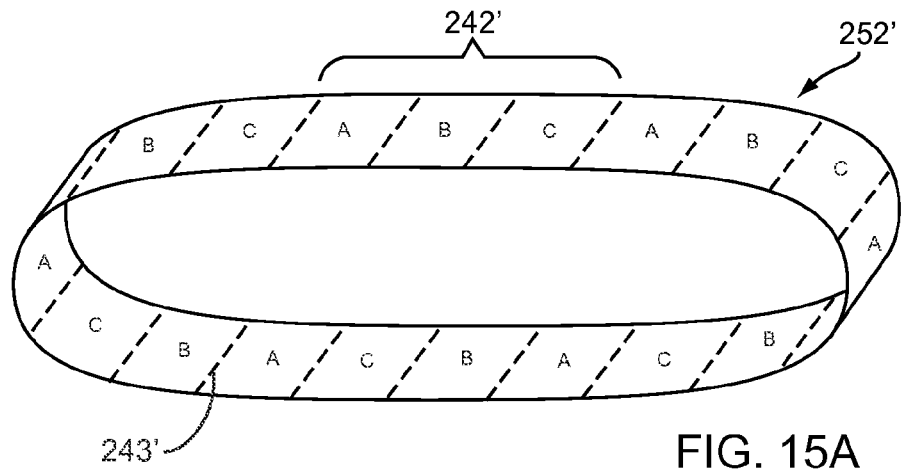
FIG. 15A is a perspective view of an alternative embodiment of a composite band including alternating sections having different material properties with edges of adjacent sections attached by orthogonal transitions.

In an alternative embodiment, shown in FIG. 15A, an endless band 252' may be formed from multiple composite sheets 242.' For example, materials A, B, C may be cut into identical sheets 242a,' 242b,' 242c' whose edges may be attached together in an alternating or sequential pattern. Thus, the sheets from each material may have the same length and width, although the lengths of the different material sheets may be different, similar to the previous embodiment. The resulting endless band 252' may be used to make multiple liner components, e.g., with the endless band 252' having a width corresponding to the individual liner components or multiple liner components.

Figure 15B:
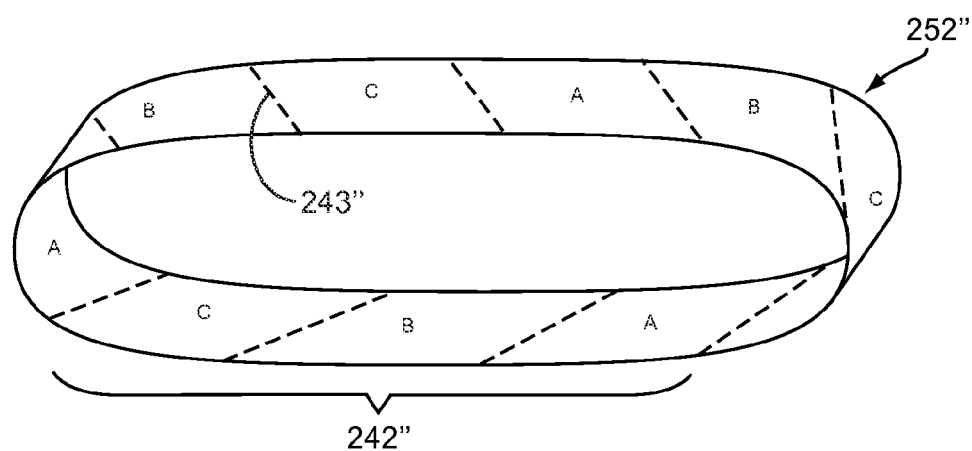
FIG. 15B is a perspective view of another alternative embodiment of a composite band including alternating sections having different material properties with edges of adjacent sections attached by non-orthogonal transitions.
Figure 15C:
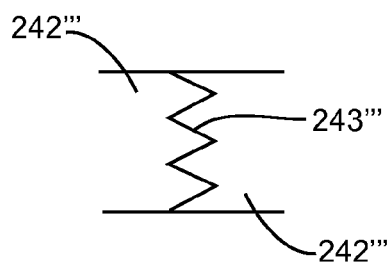
FIG. 15C is a top view of another alternative embodiment of a saw tooth seam that may be provided in a composite sheet.
Figure 15D:
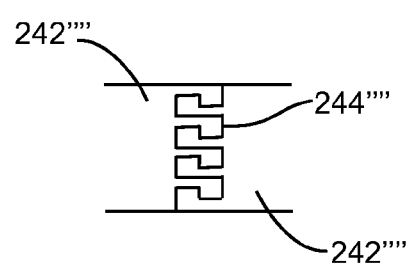
FIG. 15D is a top view of yet another alternative embodiment of an interlocked seam that may be provided in a composite sheet.

In the embodiment shown in FIG. 15A, the seams 243' between the adjacent sheets 242' may be substantially orthogonal, e.g., perpendicular, to the longitudinal edges of the endless band 252.' Alternatively, as shown in FIG. 15B, an endless band 252'' may be provided that includes multiple sheets 242'' whose adjacent edges are attached to define non-orthogonal seams 243.'' For example, the seams 243'' may extend laterally relative to the longitudinal edges of the endless band 252.'' Turning to FIG. 15C, another alternative embodiment of a seam 243''' is shown that includes a saw tooth shape, e.g., by interlocking saw tooth edges of the adjacent sheets 242.''' Finally, FIG. 15D, shows yet another alternative embodiment of an interlocked seam 243'''' that may be provided, if desired. Such non-orthogonal and/or interlocked seams may provide smoother transitions between dissimilar materials that an orthogonal seam.

Figure 13A:
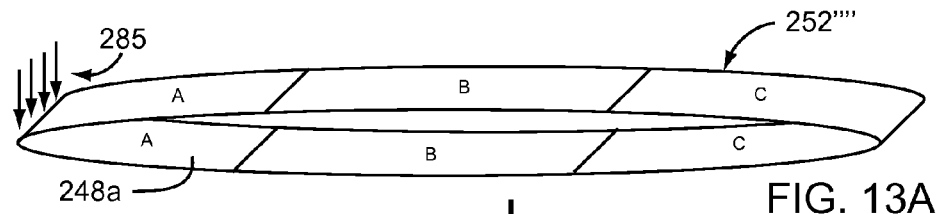
FIGS. 13A and 13B are perspective views of a composite band, e.g., formed from two sheets, such as that shown in FIG. 12D, and having a coated surface, being separated into separate relatively narrow composite bands.
Figure 13B:
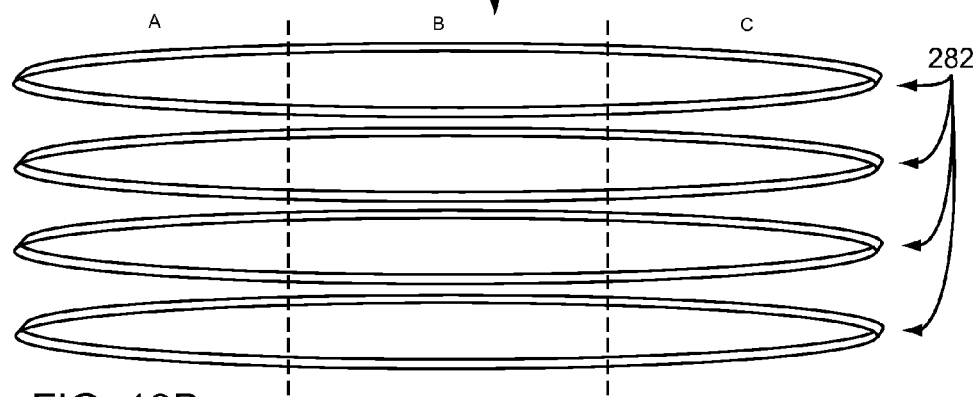

Returning to FIGS. 13A-13E, any of these composite endless bands may then be coated using any of the apparatus and methods described elsewhere herein with respect to other embodiments. For example, FIG. 13A shows an exemplary endless band 252' that has had a coating applied to its inner surface 248a. Similar to previous embodiments, the endless band 252'''' may be cut or otherwise separated into a plurality of relatively narrower endless bands 282, as shown in FIG. 13B, e.g., using cutting assembly 285 shown in FIG. 13A.

Figure 13C:
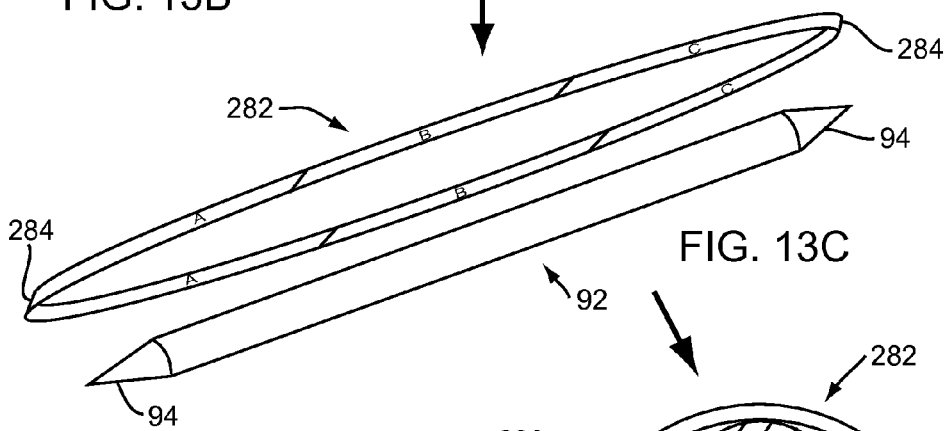
FIGS. 13C and 13D are perspective and cross-sectional views, respectively, of a relatively narrow composite band, such as those shown in FIG. 13B, being wrapped around a mandrel in a longitudinal configuration with the coated surface oriented inwardly towards the mandrel.
Figure 13D:
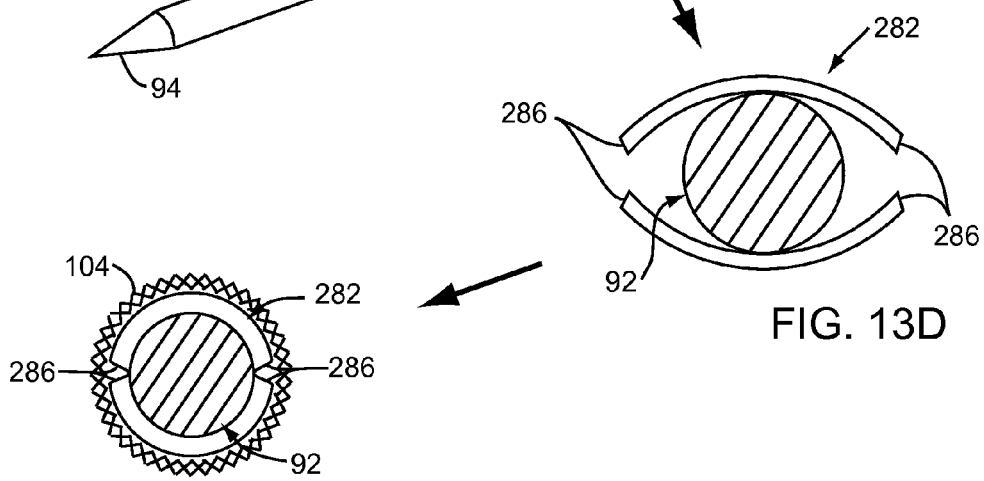
Figure 13E:
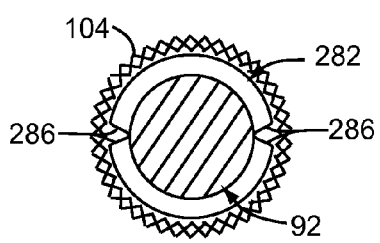
FIG. 13E is a cross-sectional view of the band and mandrel of FIGS. 13C and 13D with a reinforcing layer provided around the band.

Turning to FIGS. 13C-13E, each of the narrower endless bands 282 may be incorporated into a tubular device, similar to the previous embodiments. For example, as shown in FIG. 13C, a narrower endless band 282 may be flattened and ends 284 of the narrower endless band 282 may be received over respective ends 94 of the mandrel 92. In this embodiment, the sheets of the endless band 252'''' may be configured to ensure that the sections of the narrower endless bands 282 are symmetrical between ends 284. For example, if the intended liner includes three sections from materials A, B, C, the endless band 252'''' should include two sheets of each of these materials oriented opposite one another when the narrower endless band 282 is flattened, as shown in FIGS. 13A and 13B. As explained elsewhere herein, the sheets of the endless band 252'''' may be formed from different colors, which may facilitate identifying the transitions between the materials to confirm proper orientation of the narrower endless band 282 before being wrapped around the mandrel 92.

With particular reference to FIG. 13C, similar to the previous embodiments, the length of the flattened band 282 and the mandrel 92 may be such that the flattened band 282 may be stretched slightly to receive the ends 284 over the ends 94 of the mandrel 92, e.g., to apply a slight tension along the length of the endless band 82. As shown in FIGS. 13D and 13E, the endless band 282 may wrap around the mandrel 92 such that longitudinal edges 286 of the band 282 are disposed adjacent one another and extend substantially axially between the ends 94 of the mandrel 92. Alternatively, if desired, the ends 284 of the endless band 282 may be rotated about the longitudinal axis of the mandrel 92 relative to one another, e.g., such that the longitudinal edges 286 of the band 282 extend helically between the ends 94 of the mandrel 92 (not shown), similar to the previous embodiments.

Each narrower endless band 282 may have a width substantially half or slightly less than half the circumference of mandrel 92. Thus, the narrower endless band 282 may be wrapped around the mandrel 92 without the longitudinal edges 286 overlapping, similar to the previous embodiments. Alternatively, the width "w" of the narrower endless band 282 may be slightly smaller than half the circumference of the mandrel 92 such that a narrow gap (not shown) remains between the longitudinal edges 286 after wrapping the narrower endless band 282 around the mandrel 92 or the longitudinal edges 286 (not shown), also similar to the previous embodiments.

Turning to FIG. 13E, the narrower endless band 282, wrapped around the mandrel 92, may be incorporated into a tubular device, e.g., including a reinforcing layer 104 and an outer layer (not shown), similar to the previous embodiments.

Figure 12F:
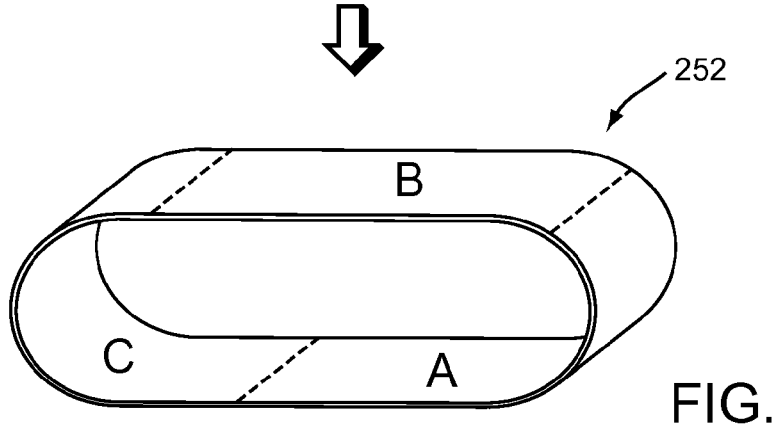
Figure 14A:
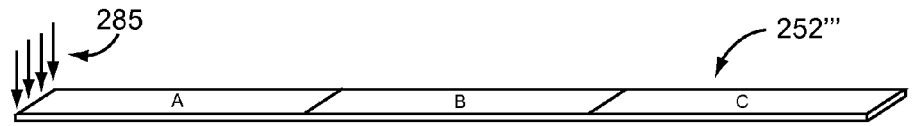
FIGS. 14A and 14B are perspective views of a composite sheet, such as that shown in FIG. 12D, being separated into separate composite strips after having a surface of the sheet coated.
Figure 14B:
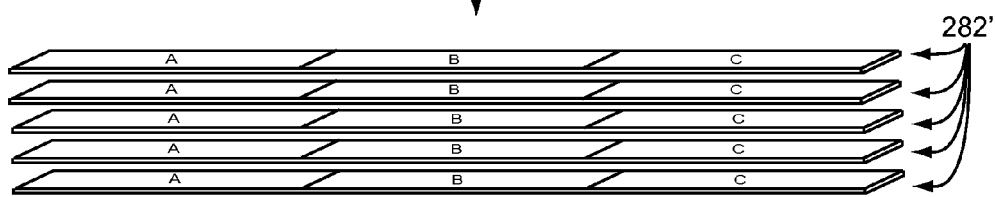

Turning to FIGS. 14A-14E, another exemplary method is shown for creating a plurality of liner components and/or tubular devices using the endless band 252 of FIG. 12F. In FIG. 14A, the endless band 252 has been cut or otherwise separated to provide a composite coated sheet 252.''' Using the cutting assembly 285, the composite coated sheet 252''' may be cut or otherwise separated into a plurality of strips 282,' e.g., as shown in FIG. 14B, which may be formed into individual liner components. If a coated endless band is created that includes multiple sequences of sheets, such as the endless band 252,' the individual sections 242' may be separated either after cutting the endless band 252' into narrower bands or after cutting across the endless band 252' to create a composite sheet (not shown), similar to FIG. 14A.

Figure 14C:
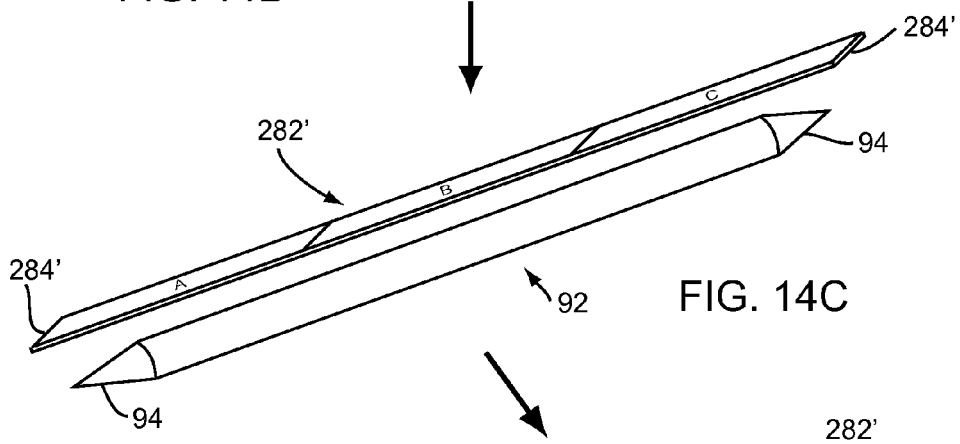
FIGS. 14C and 14D are perspective and cross-sectional views, respectively, of a composite strip, such as that shown in FIG. 14B, being wrapped around a mandrel in a longitudinal configuration with the coated surface oriented inwardly towards the mandrel.
Figure 14D:
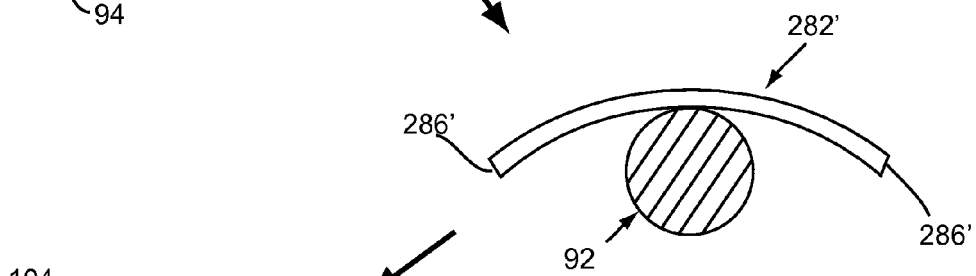
Figure 14E:
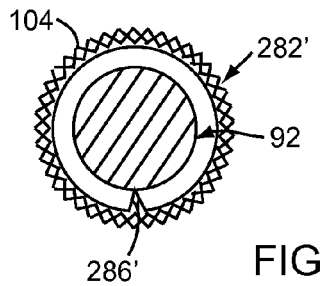
FIG. 14E is a cross-sectional view of the band and mandrel of FIGS. 14C and 14D with a reinforcing layer provided around the band.

Turning to FIGS. 14C-14E, each of the strips 282' may then be wrapped around a mandrel 92, e.g., until the longitudinal edges 286' of the strip 282' are disposed adjacent one another. For example, as shown in FIG. 14E, the inner most corners of the longitudinal edges 286' may contact one another or may be spaced slightly apart from one another (not shown), while the outer most corners of the longitudinal edges 86' are spaced apart from one another. Thus, the strip 282' may be wrapped around the mandrel 92 without the longitudinal edges 286' overlapping. Alternatively, the longitudinal edges 286' may be overlapped, if desired, similar to other embodiments herein.

Optionally, the ends 284' of the strip 282' may be secured relative to the mandrel 92, for example, by hooking the ends 284. around the ends 94 of the mandrel 92, e.g., stretching the strip 282' to apply a slight tension along the length of the strip 282.' The strip 282' wrapped around the mandrel 92 may be incorporated into a tubular device, e.g., including a reinforcing layer 104 and an outer layer (not shown), similar to the previous embodiments.

Figure 17:
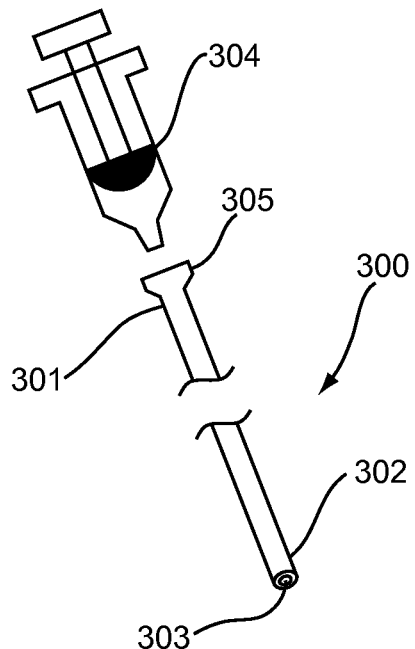
FIG. 17 is a perspective view of an exemplary embodiment of a tubular device for aspiration of material from a body lumen.

Turning to FIG. 17, an exemplary embodiment of an apparatus 300 is shown for aspiration of material (not shown) from a body lumen (not shown). The apparatus 300 includes a tubular device including a proximal end 301 and a distal end 302 sized for introduction into a body lumen. An aspiration lumen 303 extends between the proximal end 301 and the distal end 302. A vacuum source 304 may be coupled to the aspiration lumen 303 at its proximal end 301. The aspiration lumen 303 may include an inner liner (not shown) including a coating on an inner surface thereof. For example, similar to other embodiments herein, the coating may be adapted to decrease resistance to flow of aspirated material through the tubular device and/or decrease the propensity of aspirated material to clog the aspiration lumen 303. The construction of the apparatus 300, including any inner liner (not shown), may be similar to any of those described elsewhere herein. For example the apparatus 300 may include a tubular device having an outer layer (not shown) and a braided or helical reinforcing layer (not shown) surrounding the inner liner (not shown) and one or more tubular layers.

In an exemplary embodiment, the body lumen (not shown) may be a coronary artery and the material to be aspirated may be at least one of embolic material, thrombus, and plaque. Alternatively, the body lumen (not shown) may be an artery within the neurovasculature. Moreover, the body lumen (not shown) may be any vein or artery within the body, particularly one that is at least partially occluded by embolic material, thrombus and/or plaque. Alternatively, the body lumen (not shown) may be in other locations where pathologic occlusions may occur, such as the gastrointestinal or urogenital tract.

Aspiration of material from the body lumen (not shown) may be accomplished using a vacuum source 304, which may be coupled to the aspiration lumen 303 at the proximal end 301 of the tubular device. In an exemplary embodiment, the vacuum source 304 may be a syringe connected to a hub 305, for example, by means of a standard luer fitting. When a vacuum is drawn within the syringe, material (not shown) is aspirated from a body lumen (not shown), through the aspiration lumen 303, and into the syringe 304. Other sources of vacuum may include a vacuum pump, vacuum bottle, wall suction, and other suitable sources. Alternatively, the vacuum source may be made intermittent or oscillatory in order to decrease the propensity toward clogging. As a further alternative, the vacuum may be alternated with pressure for the same purpose.

As described above, the aspiration lumen 303 may include an inner liner (not show) including a coating on an inner surface thereof. For example, this coating may include a hydrophilic coating adapted to decrease friction or resistance to flow of material aspirated through the lumen 303. Other suitable coatings may be included in order to decrease resistance, increase flow rate, and/or decrease clogging of the lumen 303. For example, an anti-thrombotic coating such as heparin may be used. In addition or alternatively, a fibrinolytic coating such as streptokinase, urokinase, or tissue-type plasminogen activator may be used. Such coatings may also serve to reduce the size of aspirated particles and/or prevent particle aggregation or thrombus formation within the lumen 303. As a further alternative, the inner liner (not shown) of the aspiration lumen 303 may include multiple coatings.

Figure 18:
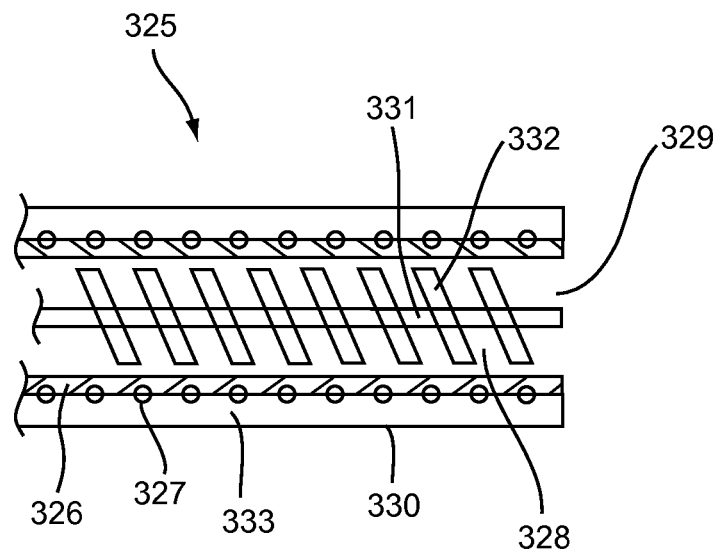
FIG. 18 is a cross-sectional view of a tubular device including a transport element.

Turning to FIG. 18, another exemplary embodiment of an apparatus 325 is shown for aspiration of material (not shown) from a body lumen (not shown). Similar to the previous embodiment, the apparatus 325 includes a tubular device including a proximal end (not shown) and a distal end 330 sized for introduction into a body lumen. An aspiration lumen 329 extends between the proximal end (not shown) and the distal end 330. The apparatus 325 may include any of the components and features described elsewhere herein with respect to other embodiments. For example, it may include an inner liner 326 including one or more coatings on the inner surface thereof, a braided or helical reinforcing layer 327 surrounding the inner liner 326, and one or more tubular layers 333. Furthermore, if desired, the apparatus 325 may include a vacuum source (not shown), which may be coupled to the proximal end, similar to the previous embodiment.

Additionally, the apparatus 325 may include a transport element, e.g. a mechanism for mechanically moving material from the distal end 330 to the proximal end (not shown), positioned within and at least partially along the length of the aspiration lumen 329. For example, the transport element may include an impeller 328 including an inner shaft 331 and a helical rotor 332, such that when rotated material is moved from the distal end 330 of the apparatus out of the body. Exemplary transport elements that may be included in the apparatus 325 and methods for making them are disclosed in U.S. Pat. Nos. 6,454,775, 6,652,548, 6,660,014, 6,663,613, 6,702,830, and 6,945,977. The entire disclosures of these references are expressly incorporated by reference herein.

Figure 19A:
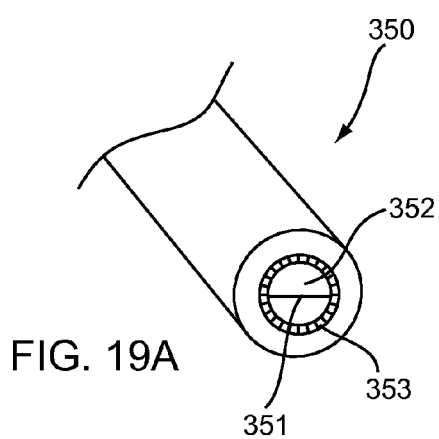
FIG. 19A is a perspective view of a tubular device including a macerating element.

Optionally, the apparatus 300 or 325 may include a macerating element. The macerating element may be passive or active. For example, turning to FIG. 19A, a wire 351 may be positioned at or near the distal end of an aspiration lumen 352 within a tubular device 350. The aspiration lumen 352 may include an inner liner 353, which may include one or more coatings on the inner surface thereof. The wire 351 may cross the diameter of the aspiration lumen 352 and may be adapted to passively cut and/or separate material as it is drawn into the lumen 352 during aspiration. The wire 351 may be positioned at the distal tip of the tubular device 350 in order to macerate material just as it enters the aspiration lumen 352. Alternatively, the wire 351 may be positioned somewhat proximal to the distal tip of the tubular device 352. Alternatively, the wire 351 may be positioned more proximally within the tubular device 350 to macerate, cut, or separate material as it passes through the lumen 352, in an effort to prevent clogging or slowing of flow. Further alternatively, multiple wires similar to 351 may be placed along the length of the tubular device 351. As a further alternatively, one or more wires 351 may be replaced by one or more blades (not shown) or other cutting elements.

Figure 19B:
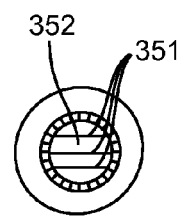
FIG. 19B is a cross-sectional view of a tubular device including multiple parallel macerating elements.
Figure 19C:
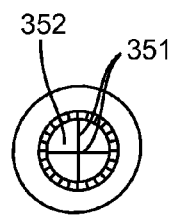
FIG. 19C is a cross-sectional view of a tubular device including multiple crossing macerating elements.
Figure 19D:
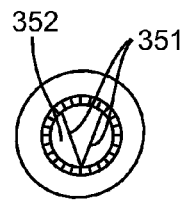
FIG. 19D is a cross-sectional view of a tubular device including multiple non-parallel macerating elements.

FIGS. 19B-D illustrate alternative configurations of wires or blades 351 that may serve to macerate material passing through an aspiration lumen. For example, two or more wires or blades 351 may be positioned substantially parallel to each other within the aspiration lumen 352, as exemplified in FIG. 19B. Alternatively, two or more wires or blades 351 may be positioned not parallel each other within the aspiration lumen 352, as exemplified in FIG. 19D. Further alternatively, two or more wires or blades may be positioned to cross one another as exemplified in FIG. 19C.

Exemplary macerating elements, including active macerating elements, that may be included in the apparatus 300 or 325 and methods for making them are disclosed in U.S. Pat. Nos. 6,454,775, 6,652,548, 6,660,014, 6,663,613, 6,702,830, and 6,945,977. The entire disclosures of these references are expressly incorporated by reference herein.

Figure 20:
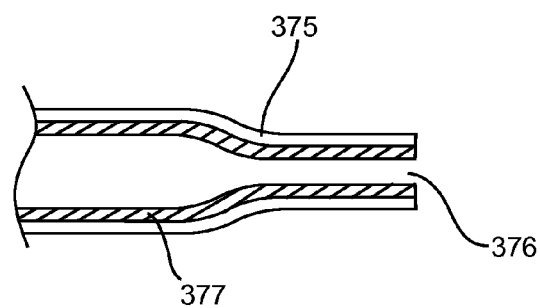
FIG. 20 is a cross-sectional view of a tubular device including a relatively smaller distal region and a relatively larger proximal region.

Turning to FIG. 20, optionally, the apparatus 300 or 325 may include a distal end 375 sized for introduction into a body lumen. An aspiration lumen 376 extends between the proximal end (not shown) and the distal end 375. The aspiration lumen 376 may include an inner liner 377 including a coating on an inner surface thereof, the coating adapted to decrease resistance to flow of aspirated material through the tubular device and/or decrease the propensity of aspirated material to clog the aspiration lumen 376. Further, the diameter of the distal end 375 and aspiration lumen 376 may vary along the length of the apparatus. For example, the most distal region of the distal end 375 may be relatively smaller than the adjacent region, e.g., to facilitate navigation through vascular anatomy, while the more proximal region of the apparatus may be relatively larger to maximize the diameter of the aspiration lumen 376 and thereby decrease resistance to flow of aspirated material through the tubular device and/or decrease the propensity of aspirated material to clog the aspiration lumen 376.

Turning to FIGS. 21A-21E, another exemplary embodiment of a method for making coated liners for tubular devices is shown. As shown, one or more liners 470 may be formed from a sleeve 450 that includes a first outer surface 452 and a second inner surface 454 that extend between a first end 456a and a second end 456b of the sleeve 450. The sleeve 450 may be formed using similar materials and/or methods to those described elsewhere herein. For example, the sleeve 450 may include urethane, nylon, engineered plastics, such as PEBAX, vestamid, and the like. The sleeve 450 may have a length corresponding to an individual coated liner or other tubular body 470 being made using the sleeve 450. Alternatively, the sleeve 450 may have a length substantially greater than an individual coated liner, e.g., such that a plurality of individual coated liners or other tubular bodies (not shown) may be made from the sleeve 450. For example, unlike the bands described elsewhere herein, the sleeve 450 may have a relatively small diameter, e.g., compared to its length (while a band may have a relatively large diameter, e.g., to facilitate accessing inner surfaces of the band).

In an exemplary embodiment, thermoplastic material may be extruded, dipped, molded, or otherwise formed and/or applied around a mandrel 440 having a desired diameter or other cross-section, e.g., corresponding to an inner diameter of a liner or other tubular device being made. The mandrel 440 may be formed from materials sufficiently durable to withstand the parameters used during manufacturing, e.g., heat and/or pressure, and/or may include a coating on its outer surface, e.g., PTFE and the like, that may facilitate removing the sleeve 450 from the mandrel 440 after processing and/or inserting the mandrel 440 through the sleeve 450 (if not formed thereon). Alternatively, the sleeve 450 may be formed separately from the mandrel 440 and the mandrel 440 may be inserted through the formed sleeve 450 to support the sleeve 450 during coating and/or other processing. In a further alternative, if the sleeve 450 is sufficiently rigid or otherwise self-supporting, the mandrel 440 may be omitted and the sleeve 450 may be processed without a supporting mandrel.

With continued reference to FIG. 21A, the first surface 452 of the sleeve 450 may be coated with a coating to impart the first surface with one or more desired properties, e.g., a hydrophilic material, an antithrombotic material, an antimicrobial material, an anti-hemolytic material, a drug-eluting material, and/or any other coating, e.g., as described elsewhere herein. For example, the sleeve 450 carried by the mandrel 440 may be dipped in or otherwise drawn through a container of liquid coating material 480. Alternatively, the sleeve 450 (with or without the mandrel 440) may be drawn upwardly through a reservoir of liquid coating material (not shown). In further alternatives, the coating may be applied using other processes, such as those described elsewhere herein, including brushing, rolling, spraying, and the like.

Turning to FIG. 21B, the coated sleeve 450 may be slit or otherwise cut between the first and second ends 456, e.g., to create a longitudinal seam, gap, or cut line 458 that extends between the first and second ends 456. For example, a blade, laser, wire, cutting wheel, heated element, or other cutter (not shown) may be directed along the sleeve 450 between the first and second ends 456 to create the seam 458. As shown, the seam 458 extends substantially parallel to a longitudinal axis of the sleeve 450, although alternatively, the seam may extend helically or otherwise between the first and second ends 456 (not shown). The seam 458 may extend partially or entirely through a wall of the sleeve 450 and/or may extend continuously or intermittently between the first and second ends 456.

The cut sleeve 460 may then be inverted, reoriented, or otherwise reversed to provide a coated reversed cut sleeve or liner 470 such that the coated first surface 452 defines an inner surface of the liner 470. For example, as shown in FIG. 21C, the cut sleeve 460 may be opened along the seam 458 such that the cut sleeve 460 includes longitudinal edges 459 that extend between the first and second ends 456. If the seam 458 is created by cutting entirely through the sleeve 450 between the first and second ends 456, opposing edges 459 may be created when the sleeve 450 is cut. Alternatively, if the seam 458 only extends partially through the wall of the sleeve 450 and/or is intermittent between the first and second ends 456, the longitudinal edges 459 may be created when the remaining material along the seam 458 is torn or otherwise separated. If the sleeve 450 is carried on a mandrel (such as mandrel 440 shown in FIG. 21A, the mandrel may be removed before, when, or after the sleeve 450 is opened.

Turning to FIG. 21D, the cut sleeve 460 may then be inverted, reoriented, or otherwise reversed to provide a coated liner 470. FIG. 21D shows an intermediate sheet 460 that is created when the opposing edges 459 of the cut sleeve 460 have been completely separated. The sheet 460 may be rolled around a mandrel (not shown) or other device to create the reversed cut sleeve or liner 470 shown in FIG. 21E. Alternatively, the cut sheet 460 may be separated into a plurality of strips (not shown), e.g., similar to other embodiments herein, and individual strips may be rolled around a mandrel to provide a coated liner. Optionally, if desired, the opposing edges 459 of the liner 470 may be attached together to provide a substantially enclosed sleeve or tube (not shown). Alternatively, the opposing edges 459 may remain free but adjacent to one another, e.g., abutting, overlapping, or spaced slightly apart, before being incorporated into other devices, similar to other embodiments described elsewhere herein.

Figure 22:
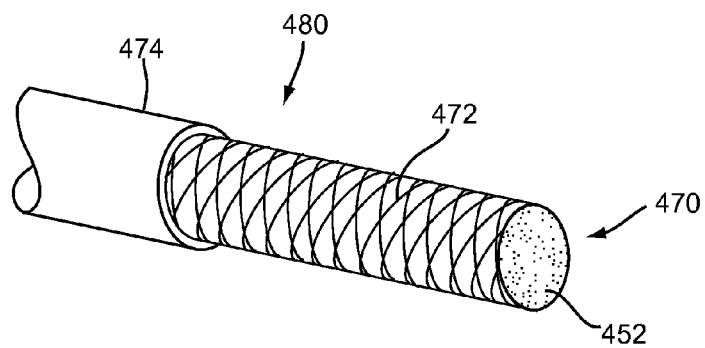
FIG. 22 shows an outer layer being applied around the liner component of FIG. 21E.

The resulting coated liner 470 (whether with separate edges or formed into an enclosed sleeve) may be incorporated into one or more tubular bodies, e.g., one or more catheter or lead bodies, similar to other embodiments described elsewhere herein. For example, as shown in FIG. 22, a tubular structure may be attached around the liner 470, thereby providing a tubular device 480 including an inner surface 452 with a hydrophilic and/or other coating. For example, in one embodiment, the liner 470 may be positioned over a mandrel (not shown) such that the opposing edges 459 (see FIG. 21D) are disposed adjacent one another, and one or more layers 472, 474 may be applied around the liner 470 to provide the tubular device 480.

As shown in FIG. 22, a reinforcing layer 472 has been applied around the coated liner 470 and an outer layer 474 is being positioned over the reinforcing layer 472 and liner 470. In an exemplary embodiment, the reinforcing layer 472 may be wrapped around the liner 470 and mandrel (not shown), and the resulting assembly may be heated, e.g., using heat shrink tubing, direct hot air, a heated external die, and the like (not shown) to at least partially reflow the material of the liner 470, e.g., to embed the reinforcing layer 472 partially in the liner 470 and/or otherwise bond the reinforcing layer to the liner 470.

The resulting subassembly may be stored for subsequent use or may have a tubular structure 474, e.g., including one or more solid wall layers, positioned over and attached to the reinforcing layer 472 and coated liner 470. For example, an enclosed tubular structure 474 may be inserted over the reinforcing layer 472 and liner 470 or one or more layers of material may be wrapped or otherwise built up to provide the outer layer 474. The resulting assembly may be heated, e.g., to at least partially reflow the material of the liner 470 and/or the outer layer 474, may be bonded with adhesive, and the like to provide the tubular device 480.

Figure 23:
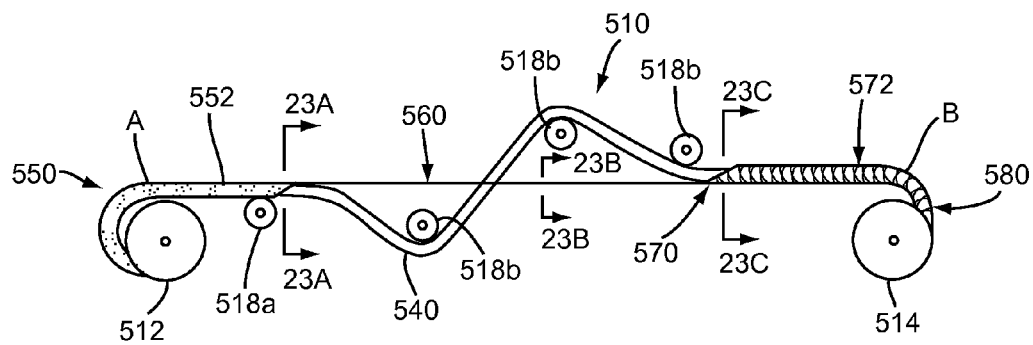
FIG. 23 is a schematic showing an exemplary apparatus and method for substantially continuously making coated liners by reversing external coated surfaces of a liner substrate.

Turning to FIG. 23, an apparatus 510 is shown for making tubular devices including coated inner surfaces, e.g., similar to the coated liner 470, although using a substantially continuous process. As shown, the apparatus 510 includes a supply reel 512 for providing a sleeve 550 or other length of tubular supply material, e.g., on a mandrel 540, an uptake reel 514 for receiving the finished coated liner 570 or other tubular device(s) 580, a slitter or other cutter 516 (shown in FIG. 23A) for cutting the sleeve 550, e.g., after coating, and a plurality of rollers or other guides 518 for directing the sleeve 550 and/or mandrel 540 along the apparatus 510 and/or maintaining sufficient tension to ensure substantially continuous operation of the apparatus 510.

Figure 23A:
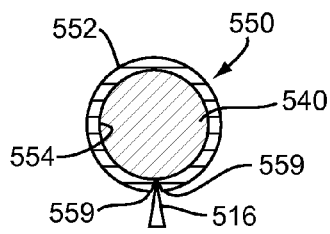
FIGS. 23A-23C are cross-sectional details of the coated liner at different stages in the apparatus and method of FIG. 23.

Similar to the previous embodiment, the sleeve 550 may include a first outer surface 552 and a second inner surface 554 that extend between ends of the sleeve 550 (best seen in FIG. 23A). As shown, the sleeve 550 is initially provided on a mandrel 540 to provide a sleeve subassembly, and the sleeve subassembly is carried by the supply reel 512 or other supply source (not shown). Alternatively, if the sleeve 550 has sufficient rigidity or self-supporting structure, the mandrel 540 may be eliminated and the sleeve 550 may be drawn from the supply reel 512 on its own. In one embodiment, the first surface 552 of the sleeve 550 may be coated with a coating, e.g., before being loaded onto the supply reel 512, as shown. Alternatively, the first surface 552 may be coated after the sleeve or sleeve subassembly is directed from the supply reel 512, e.g., at location "A," which is identified schematically and not necessarily spatially in FIG. 23. In this alternative, the apparatus 510 may include one or more sprayers, dipping tanks, and the like (not shown) that may be used to apply a coating to the first surface 552 and, optionally, one or more curing devices, e.g., heaters, UV light sources, and the like (also not shown), that may apply and/or cure the coating on the first surface 552 between the supply reel 512 and the cutter 516, similar to other embodiments described elsewhere herein.

At location 23A-23A in FIG. 23, the coated sleeve 550 may be cut along its length to create a longitudinal seam defined by opposing edges 559 that extends substantially continuously along the length of the coated sleeve 550. For example, as shown in FIG. 23A, a cutter 516, e.g., a blade, laser, wire, cutting wheel, heated element, and the like, may be provided for creating a substantially continuous seam along the coated sleeve 550. In one embodiment, the cutter 516 may be incorporated into roller 518a shown in FIG. 23, although alternatively, a separate cutter may be provided adjacent roller 518a (not shown in FIG. 23).

Figure 23B:
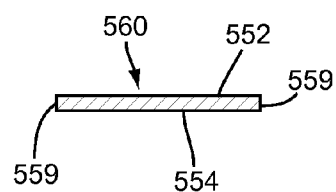

The apparatus 510 may include multiple rollers 518b, which may facilitate separating the cut sleeve 560 from the mandrel 540, as shown in FIG. 23. For example, the apparatus 510 may maintain sufficient tension to automatically open the cut sleeve 560 into a substantially planar strip, as best seen in FIG. 23B, while directing the mandrel 540 out of and away from the cut sleeve 560. Although not shown, the apparatus 510 may include a set of rollers or other tensioning devices to maintain sufficient tension on the sleeve 550 and/or mandrel 540 as they are directed along the apparatus 510, similar to other embodiments described elsewhere herein.

Figure 23C:
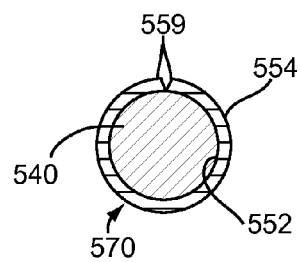

At location 23C-23C in FIG. 23, the mandrel 540 and cut sleeve 560 may again be merged together, e.g., such that the cut sleeve 560 may be positioned around the mandrel 540 to provide an reversed cut sleeve or coated liner 570. For example, the apparatus 510 may cause the cut sleeve 560 to wrap automatically around the mandrel 540, e.g., by applying a desired tension, such that the coated first surface 552 is oriented inwardly towards the mandrel 540 and the opposing edges 559 are disposed adjacent one another, as best seen in FIG. 23C. Thus, the cut sleeve 560 may provide a coated liner 570 around the mandrel 540, similar to the coated liner 470, although liner 570 may have a length substantially longer than the liner 470.

Optionally, a reinforcing layer 572 may be applied around the coated liner 570, e.g., before the liner 570 is wound onto uptake reel 514. For example, a braiding device (not shown) may be provided for applying multiple strands helically or otherwise around the liner 570, which may facilitate constraining the liner 570 around the mandrel 540. Exemplary apparatus and methods for wrapping reinforcing layers around sleeves or strips are disclosed in U.S. Publication No. 2009/0126862, incorporated by reference herein. Optionally, at location "B" in FIG. 23 (which is again identified schematically and not necessarily spatially relative to other components of the apparatus 510), one or more additional layers may be applied around the reinforcing layer 572 and/or other processing may be completed, similar to the other embodiments described elsewhere herein. The resulting tubular device 580 may be wound onto uptake reel 514, e.g., for further processing and/or incorporation into one or more tubular devices. For example, the tubular device 580 may be cut into individual tubular bodies and/or may have one or more components added (not shown) to provide a finished catheter, lead, or other tubular device, similar to other embodiments described elsewhere herein.

Figure 24:
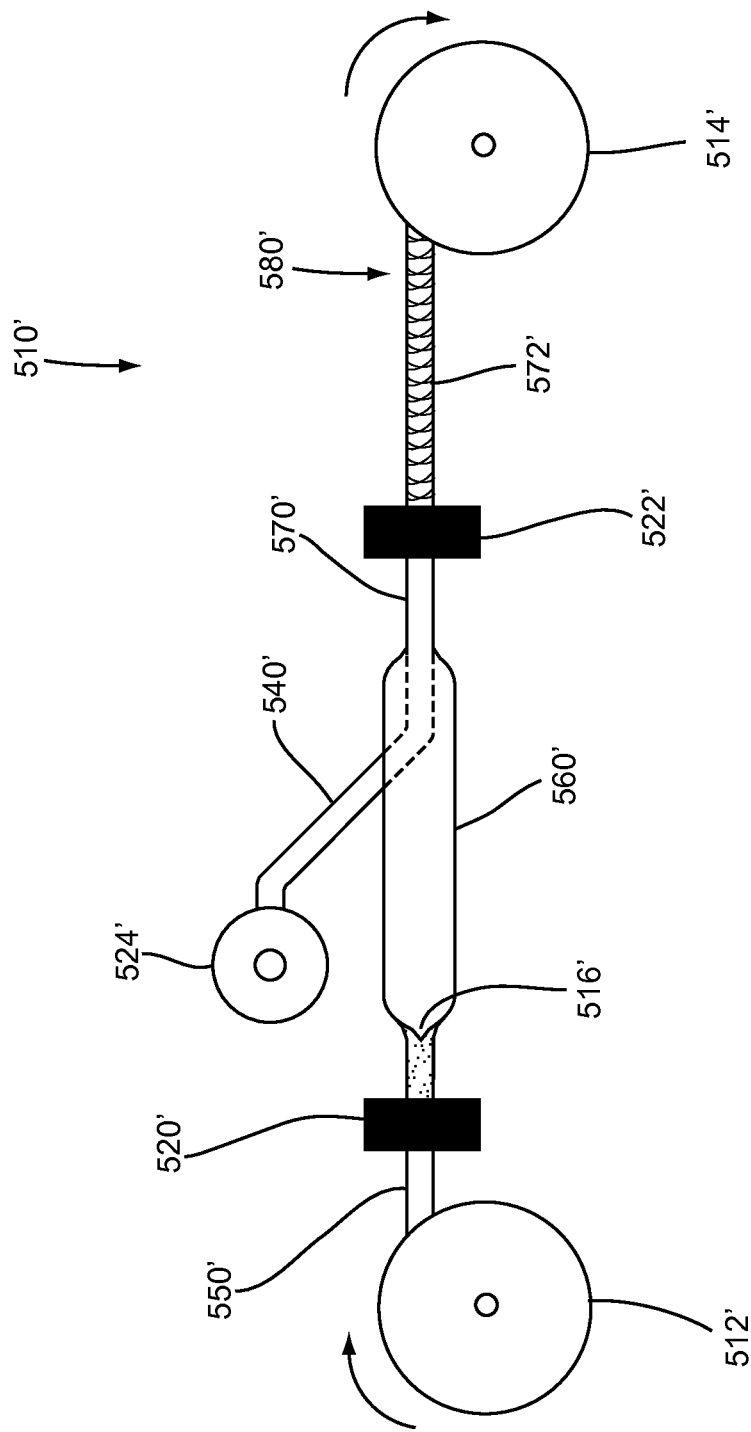
FIG. 24 is a schematic showing another exemplary apparatus and method for substantially continuously making coated liners by reversing external coated surfaces of a liner substrate.

Alternatively, separate mandrels may be provided for the sleeve 550 originating from the supply reel 512 and the coated liner 570 or tubular device 580 collected by the uptake reel 514. For example, FIG. 24 shows an apparatus 510' that is generally similar to the apparatus 510 (where similar elements are identified by similar numbers except with a' added). Unlike the apparatus 510, however, a mandrel is not shown being removed from the sleeve 550' after it is cut by cutter 516.' For example, the sleeve 550' may be provided on supply reel 512' without a mandrel, although, alternatively, the sleeve 550' may be carried by a separate mandrel than mandrel 540' or may be carried by the same mandrel 540' being separated from and merged again with the sleeve 550,' similar to the previous embodiment.

Optionally, the supply and uptake mandrels may have different diameters or other cross-sections (not shown). For example, the uptake mandrel may have a larger diameter than the supply mandrel, e.g., to provide a gap between the opposing edges 559 of the reversed cut sleeve or coated liner 570 when wrapped around the mandrel 540 (see FIG. 24C), or to allow multiple sleeves being fed around a single mandrel to provide a single liner, e.g., similar to other embodiments described elsewhere herein.

In addition, apparatus 510' in FIG. 24 includes one or more coating devices 520' (one shown schematically), e.g., similar to the previous embodiments. Thus, the sleeve 550' may be uncoated when wound onto supply reel 512' and coated before being cut by cutter 516.' If the sleeve 550' is carried on a mandrel (not shown) from the supply reel 512,' the mandrel may be removed after applying the coating with the coating device(s) 520,' e.g., after cutting the sleeve 550' with the cutter 516,' similar to the previous embodiment, but may be discarded or reused. Mandrel 540' may be carried on a mandrel reel 524' from which the mandrel 540' may be fed substantially continuously towards the cut sleeve 560' such that the reversed cut sleeve or coated liner 570' is wrapped around the mandrel 540,' similar to the previous embodiments. As shown, the apparatus 510' also includes a braiding device 522,' which may wrap a reinforcing layer 572' around the coated liner 570,' e.g., similar to other embodiments herein, to provide a tubular body 580,' which may be captured on uptake reel 514.' The resulting tubular body 580' may be wound onto the uptake reel 514' for subsequent processing and/or incorporation into one or more tubular devices, similar to the previous embodiments.

Figure 25A:
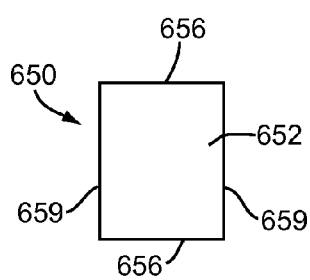
FIGS. 25A-25E are side views showing a method for making a coated liner from a sheet carried by a mandrel.

Turning to FIGS. 25A-25E, alternative methods are shown for making coated liners, e.g., for catheters, leads, or other tubular devices. Generally, as shown in FIG. 25A, a sheet 650 may be initially provided that includes an outer first surface 652, an inner second surface 654, and longitudinal edges 659 extending between first and second ends 656. The sheet 650 may be formed from thermoplastic or other material, such as those described elsewhere herein.

Figure 25B:
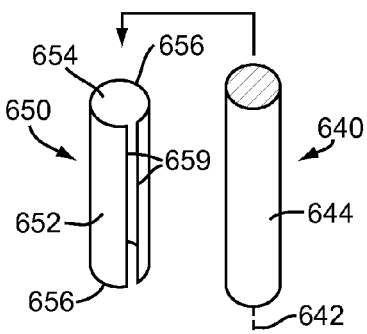
Figure 25C:
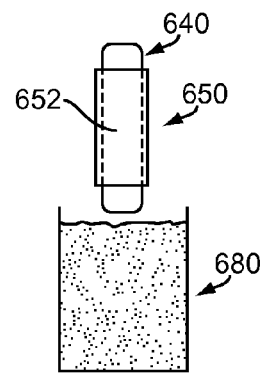
Figure 26A:
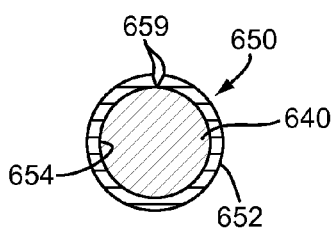
FIGS. 26A-26C are cross-sectional views of alternative embodiments of mandrels that may be used to coat a sheet using the method of FIGS. 25A-25E.

As shown in FIGS. 25B and 25C, the sheet 650 may be secured around a mandrel 640, e.g., such that the longitudinal edges 659 extend along a longitudinal axis 642 of the mandrel 640 and the first surface 652 is disposed outwardly. For example, as shown in FIG. 26A, the mandrel 640 may be a solid or hollow tubular body and the sheet 650 may be wrapped around the outer surface 644 of the mandrel 640. The sheet 650 may be secured to the outer surface 644 of the mandrel 640 using one or more features, such as one or more bands, clips, and the like (not shown). In addition or alternatively, the sheet 650 may be secured using a low tack adhesive or other material (not shown) applied to the outer surface 644 of the mandrel 640 and/or to the second surface 654 of the sheet 650 and/or at one or more locations along the longitudinal edges 659.

Figure 26B:
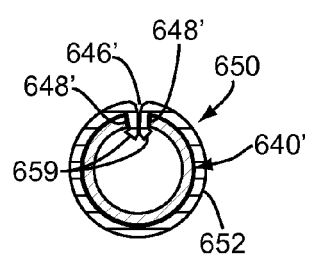

In an alternative embodiment, shown in FIG. 26B, a mandrel 640' may be provided that includes one or more slots for capturing the longitudinal edges 659 of the sheet 650. As shown, the mandrel 640' has a "C" shaped cross-section, thereby defining a longitudinal slot 646' defined by opposing edges 648' that extend longitudinally along the mandrel 640.' The mandrel 640' may be biased such that the edges 648' abut or are closely spaced apart from one another, yet the mandrel 640' may be sufficiently flexible to allow the edges 648' to be moved apart from one another. For example, the edges 648' may be moved apart to open the slot 646,' whereupon the longitudinal edges 659 of the sheet 650 may be introduced into the slot 646.' When the edges 648' of the mandrel 640' are then released, the edges 648' may engage the longitudinal edges 659 of the sheet 650, thereby securing the sheet 659 around the mandrel 640.'

Figure 26C:
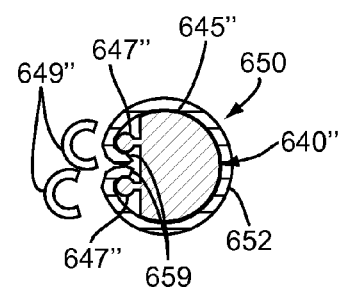

In a further alternative, shown in FIG. 26C, a mandrel 640" may be provided that includes a convex surface region 645" and a pair of ridges 647" sized to be engaged by clips 649." The ridges 647" may extend substantially parallel to a longitudinal axis of the mandrel 640," e.g., opposite the convex surface region 645." For example, as shown, the sheet 650 may be wrapped around the convex surface region 645" of the mandrel 640" such that the longitudinal edges 659 of the sheet are disposed over the ridges 647." The clips 649" may be then be snapped or otherwise placed over the ridges 647" to capture the longitudinal edges 659 of the sheet 650 therebetween, thereby securing the sheet 659 to the mandrel 640." Thus, in any of these alternatives, the sheet 650 may be secured to a mandrel 640 sufficiently tightly such that the first surface 652 of the sheet 650 is substantially smooth to accommodate receiving a coating.

Figure 25D:
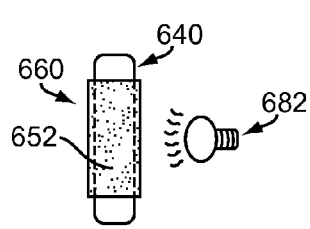

Turning to FIG. 25C, after securing the sheet 650 to the mandrel 640 (or the other mandrels just described), a coating may be applied to the first surface 652 of the sheet 650. For example, as shown, the assembly of the sheet 650 and mandrel 640 may be dipped in a reservoir of liquid coating material 680 to apply the liquid coating material to the first surface 650. Alternatively, the coating may be applied using other processes, such as spraying, brushing, rolling, and the like, similar to other embodiments herein. As shown in FIG. 25D, the coating material may be cured, e.g., exposure to ultraviolet light 682, heating, air drying, and the like, similar to other embodiments herein.

Figure 25E:
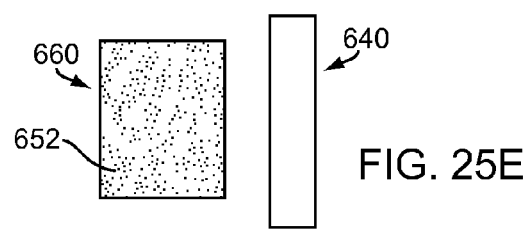

Turning to FIG. 25E, once the coating is cured, the coated sheet 660 may then be removed from mandrel 640. The coated sheet 660 may then be oriented with the coated first surface 652 disposed inwardly to provide one or more coated liners (not shown), similar to other embodiments described elsewhere herein. If the coated sheet 660 includes uncoated regions, e.g., adjacent the longitudinal edges 659 due to being captured by the mandrel 640,' 640," the uncoated regions may be cut off or otherwise removed if desired. Alternatively, the uncoated edges 659 may be attached together, e.g., by lapping or butting the edges 659 similar to other embodiments herein, to provide an enclosed sleeve with a longitudinal seam (not shown).

Figure 27A:
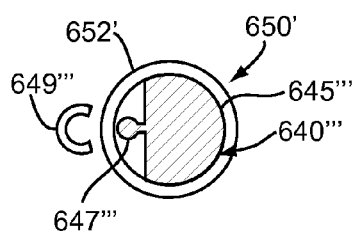
FIGS. 27A and 27B are cross-sectional views showing a tubular sleeve being secured to a mandrel for making a coated liner using a method similar to the method of FIGS. 25A-25E.
Figure 27B:
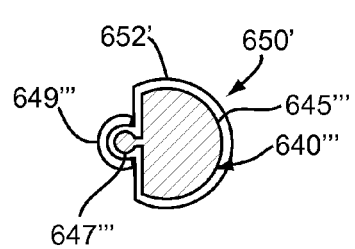

Alternatively, as shown in FIGS. 27A and 27B, an enclosed tube or sleeve 650' may be secured to a mandrel 640' to facilitate coating a first surface 652' of the sleeve 650.' The sleeve 650' may be formed using materials and/or methods similar to any of the embodiments described elsewhere herein, e.g., including a longitudinal seam (not shown). The mandrel 640'" may include a convex outer surface 645' opposite a ridge or other feature 647' that extend longitudinally along the mandrel 640.'" The sleeve 650' may be received around the mandrel 640' and a clip 649' may be snapped or otherwise received over the ridge 647' to capture the sleeve 650' therebetween, thereby securing the sleeve 650' to the mandrel 640' and/or providing sufficient tension on the sleeve 650' to facilitate coating the first surface 652.' The sleeve 650' may then be coated and separated from the mandrel 640' similar to the previous embodiment. The coated sleeve 650' may then be reversed, or cut or otherwise separated into one or more coated sheets, similar to other embodiments herein.

Optionally, similar to other embodiments herein, the reversed coated sheet 660 (or coated sleeve 650') may be incorporated into one or more tubular devices. For example, similar to other embodiments herein, the coated sheet 660 of FIG. 25E may be wrapped around a mandrel (either the same or different than mandrel 640), except with the coated surface 652 oriented inwardly. One or more layers, e.g., a reinforcing layer, and/or outer tubular structure may be positioned and attached around the coated sheet 660 to provide a catheter component, similar to the previous embodiments.

Turning to FIGS. 28A-28D, another exemplary method is shown for making coated liners using a mandrel 740 including first and second ends 741 and an outer surface 744. The mandrel 740 may be a solid or tubular body, e.g., having a cylindrical or other cross-section. The outer surface 744 may include a surface finish or coating to facilitate holding coating material thereon without allowing the coating material to bond substantially to the outer surface 744.

As shown in FIG. 28A, the mandrel 740 may be dipped in a reservoir of liquid coating material 780 to apply coating material 784 to the outer surface 744 of the mandrel 740, as shown in FIG. 28B. Alternatively, the coating material 784 may be applied using other methods, such as spraying, rolling, brushing, and the like, similar to other embodiments herein.

Turning to FIG. 28B, after applying the coating material, a substrate 750 may be positioned over the mandrel 740 such that a first surface 752 of the substrate 750 contacts the coating material 784. For example, the substrate 750 may be a sheet made from thermoplastic or other material similar to other embodiments herein that is wrapped around the mandrel 740 such that longitudinal edges (not shown) of the sheet are disposed adjacent one another. Alternatively, the substrate 750 may be an enclosed sleeve, which may be positioned around the mandrel 740 and then shrunk, e.g., by heating, to cause the first surface 752 to contact the coating material 784 and outer surface 744 of the mandrel 740.

Turning to FIG. 28C, with the substrate 750 positioned over the mandrel 740, the coating material 784 may be cured through the substrate 750 such that the coating material 784 bonds to the first surface 752 to provide a coating having one or more desired properties, such as those described elsewhere herein. For example, as shown, a source of ultraviolet light 782 may be provided adjacent the substrate 750 to at least partially cure the coating material 784. The substrate 750 may be at least partially transparent to the ultraviolet light such that at least some of the ultraviolet light passes through the substrate 750 to at least partially cure the coating material 784. In addition or alternatively, other processes may be used to cure the coating material 784 and/or bond the coating material 784 to the first surface of the substrate 750. For example, shrink tubing (not shown) may be positioned around the substrate 750 and heat may be applied to heat the shrink tubing, substrate 750, and consequently the coating material 784. The shrink tubing may also attempt to shrink when heated, thereby applying inward pressure against the substrate 750 to enhance curing and/or bonding. In another option, vacuum may be applied, e.g., through one or more ports in the outer surface 744 of the mandrel 740 to enhance apposition of the substrate 750 against the coating material 784 and outer surface 744.

Turning to FIG. 28D, the mandrel 740 may then be removed from the substrate to provide a coated liner 770 having a coated inner surface 752. For example, once the coating material is cured, the mandrel 740 may simply be slid out of the substrate 750, e.g., if the substrate 750 is a sleeve. Alternatively, if the substrate 750 is a sheet, the sheet may be unwrapped from the mandrel 740. Optionally, similar to previous embodiments, one or more layers may be applied around the coated liner 770, e.g., before or after removing the mandrel 740 to provide one or more tubular bodies.

Turning to FIGS. 29A-29C, an alternative embodiment is shown for creating a coating liner 870 by applying coating material 884 to a mandrel 840. Unlike the previous embodiment, the mandrel 840 may be a plate including an outer surface 844, which may have a convex shape as shown, or alternatively, a concave, multiple curve, or substantially flat shape (not shown). As shown in FIG. 29A, coating material 884 may be applied to the outer surface 844, and then a substrate 850, e.g., a sheet, may be positioned against the mandrel 840 such that a first surface 852 of the substrate contacts the coating material 884 and outer surface 844, as shown in FIG. 29B. The coating material 884 may be cured and/or bonded to the first surface 852 of the substrate 850, and then the coated substrate 870 may be removed from the mandrel 840 to provide a coated liner, which may be incorporated into one or more tubular devices, similar to the previous embodiments.

In still another alternative, a sleeve or otherwise shaped reservoir of substrate material may have one end sealed (not shown), and the sleeve may be filled with liquid coating material. If the sleeve is at least partially transparent to ultraviolet light, ultraviolet light may be delivered through the sleeve to at least partially cure the coating material and/or bond the coating material to an inner surface of the sleeve. Once sufficiently cured, any remaining coating material may be removed, and the resulting sleeve may be incorporated into one or more tubular device, similar to the previous embodiments.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for making a catheter or sheath sized for introduction into a body lumen, comprising:
   providing a sleeve comprising an outer first surface and an inner second surface extending between a first end and a second end;
   coating the first surface with a coating to impart the first surface with one or more desired properties;
   cutting the coated sleeve between the first and second ends to create opposing edges extending between the first and second ends;
   reversing the cut sleeve such that the coated first surface defines an inner surface of the reversed cut sleeve and the opposing edges are disposed adjacent one another to provide a coated liner;
   attaching a tubular structure around the coated liner, thereby providing a tubular device comprising an inner surface with the one or more desired properties; and
   attaching a handle or hub to one end of the tubular device,
   further comprising maintaining tension on the sleeve by directing the sleeve along a plurality of rollers or other guides during the cutting and reversing steps.

2. The method of claim 1, wherein attaching a tubular structure around the coated liner comprises:
   positioning the coated liner over a mandrel such that the opposing edges are disposed adjacent one another;
   positioning the tubular structure over the coated liner; and
   attaching the tubular structure to the coated liner.

3. The method of claim 2, further comprising removing the mandrel after attaching the tubular structure to the coated liner.

4. The method of claim 2, wherein positioning the tubular structure over the coated liner comprises:
   applying a reinforcing layer around the coated liner; and
   applying one or more layers of material around the reinforcing layer.

5. The method of claim 4, wherein the reinforcing layer comprises at least one of a braided structure and a helical structure.

6. The method of claim 4, further comprising heating at least one of the reinforcing layer and the coated liner after applying the reinforcing layer and before applying the one or more layers of material around the reinforcing layer, to attach the reinforcing layer to the coated liner.

7. The method of claim 6, wherein the sleeve comprises thermoplastic material such that the coated liner reflows at least partially into the reinforcing layer during the heating step.

8. The method of claim 1, wherein the coating comprises at least one of hydrophilic material, an antithrombotic material, an antimicrobial material, an anti-hemolytic material, and a drug-eluting material.

9. The method of claim 1, wherein the tubular structure is attached to the coated liner using at least one of heat bonding, adhering with one or more adhesives, and reflowing the tubular structure.

10. The method of claim 1, further comprising attaching the opposing edges of the reversed cut to create a seam that extends between the first and second ends of the coated liner before attaching the tubular structure.

11. The method of claim 1, wherein the sleeve defines a longitudinal axis that extends between the first and second ends, and wherein the coated sleeve is cut longitudinally such that the opposing edges extend substantially parallel to the longitudinal axis.

12. The method of claim 1, wherein the sleeve is initially provided on a first mandrel before the coated sleeve is cut, and wherein the first mandrel is removed before reversing the cut sleeve.

13. The method of claim 12, wherein the sleeve is initially provided on the mandrel by extruding sleeve material onto the mandrel.

14. The method of claim 12, wherein reversing the cut sleeve comprises positioning the cut sleeve around a second mandrel with the coated first surface disposed inwardly towards the second mandrel before attaching the tubular structure around the coated liner.

15. A method for making tubular devices sized for introduction into a body lumen, comprising:
   providing a thin-walled sleeve comprising an outer first surface and an inner second surface extending between a first end and a second end;
   coating the first surface with a coating to impart the first surface with one or more desired properties;
   cutting the coated sleeve between the first and second ends to create opposing edges extending between the first and second ends;
   opening the coated sleeve by separating the opposing edges; and
   positioning the cut sleeve around an uptake mandrel to reverse the cut sleeve such that the coated first surface is oriented inwardly towards the uptake mandrel and the opposing edges are disposed adjacent one another, thereby providing a coated liner,
   wherein the cutting, opening, and positioning steps are completed using a substantially continuous process,
   further comprising maintaining tension on the sleeve by directing the sleeve along a plurality of rollers or other guides during the cutting, opening, and positioning steps.

16. The method of claim 15, further comprising attaching a tubular structure around the coated liner, thereby providing a tubular device comprising an inner surface with the one or more desired properties.

17. The method of claim 15, wherein the coating comprises at least one of hydrophilic material, an antithrombotic material, an antimicrobial material, an anti-hemolytic material, and a drug-eluting material.

18. The method of claim 1, wherein coating the first surface comprises drawing the sleeve through a liquid coating material such that the first surface is exposed to the liquid coating material.

19. The method of claim 18, wherein coating the first surface further comprises curing the liquid coating material such that the coating is bonded to the first surface.

20. The method of claim 15, further comprising attaching the opposing edges of the reversed cut sleeve to create a seam that extends between the first and second ends.

21. The method of claim 1, wherein the tubular device includes a proximal end, a distal end sized for introduction into a patient's body, and a length therebetween sufficient such that the distal end may be introduced into a target location within a patient's body while the proximal end remains outside the patient's body.

22. A method for making a catheter or sheath sized for introduction into a body lumen, comprising:

providing a sleeve comprising an outer first surface and an inner second surface extending between a first end and a second end;

coating the first surface with a coating to impart the first surface with one or more desired properties;

cutting the coated sleeve between the first and second ends to create opposing edges extending between the first and second ends;

reversing the cut sleeve such that the coated first surface defines an inner surface of the reversed cut sleeve and the opposing edges are disposed adjacent one another to provide a coated liner;

thereafter, attaching a tubular structure around the coated liner, thereby providing a tubular device comprising an inner surface with the one or more desired properties; and attaching a handle or hub to one end of the tubular device, further comprising maintaining tension on the sleeve by directing the sleeve along a plurality of rollers or other guides during the cutting and reversing steps.

23. The method of claim 1, wherein the sleeve is directed along a plurality of rollers or other guides for maintaining sufficient tension during the reversing step.

* * * * *